US008961503B2

(12) United States Patent
Lau et al.

(10) Patent No.: US 8,961,503 B2
(45) Date of Patent: Feb. 24, 2015

(54) APPARATUS AND METHOD FOR REGULATING TISSUE WELDER JAWS

(71) Applicant: MAQUET Cardiovascular LLC, San Jose, CA (US)

(72) Inventors: Liming Lau, Mountain View, CA (US); Arnold M. Escano, Santa Clara, CA (US); Jerry Jarrard, Sunnyvale, CA (US); Sam Ho, Fremont, CA (US); Ryan C. Abbott, San Jose, CA (US); Arthur M. Lin, Fremont, CA (US); Jesse McQuiston, Palo Alto, CA (US); Peter L. Callas, Castro Valley, CA (US); Geoffrey H. Willis, Redwood City, CA (US); Michael C. Stewart, San Jose, CA (US); Kimberly D. Barkman, Redwood City, CA (US); Joseph N. Lamberti, Castro Valley, CA (US); Kenny L. Dang, San Jose, CA (US)

(73) Assignee: MAQUET Cardiovascular LLC, Mahwah, NJ (US)

( * ) Notice: Subject to any disclaimer, the term of this patent is extended or adjusted under 35 U.S.C. 154(b) by 0 days.

(21) Appl. No.: 14/148,671

(22) Filed: Jan. 6, 2014

(65) Prior Publication Data
US 2014/0194876 A1 Jul. 10, 2014

Related U.S. Application Data

(63) Continuation of application No. 13/549,367, filed on Jul. 13, 2012, now Pat. No. 8,623,003, which is a continuation of application No. 13/047,778, filed on Mar. 14, 2011, now abandoned, which is a continuation of application No. 11/090,330, filed on Mar. 25, 2005, now Pat. No. 7,918,848.

(51) Int. Cl.
*A61B 18/04* (2006.01)
*A61B 18/08* (2006.01)
(Continued)

(52) U.S. Cl.
CPC ....... *A61B 18/085* (2013.01); *A61B 2017/3445* (2013.01); *A61B 2017/2912* (2013.01);
(Continued)

(58) Field of Classification Search
USPC ..................................... 606/27–34
See application file for complete search history.

(56) References Cited

U.S. PATENT DOCUMENTS

| 2,137,710 A | 11/1938 | Anderson |
| 4,031,898 A | 6/1977 | Hiltebrandt et al. |

(Continued)

FOREIGN PATENT DOCUMENTS

| DE | 10328514 B3 | 3/2005 |
| EP | 0538984 B1 | 3/1997 |

(Continued)

OTHER PUBLICATIONS

PCT International Search Report, PCT/US2006/010569, mailed Jul. 24, 2006, 8 pages.

(Continued)

*Primary Examiner* — Lee S Cohen

(57) ABSTRACT

A surgical apparatus and methods for severing and welding tissue, in particular blood vessels. The apparatus includes an elongated shaft having a pair of relatively movable jaws at a distal end thereof. A first heating element on one of the jaws is adapted to heat up to a first temperature and form a welded region within the tissue, while a second heating element on one of the jaws is adapted to heat up to a second temperature and sever the tissue within the welded region. The first and second heating elements may be provided on the same or opposite jaws. A control handle provided on the proximal end of the elongated shaft includes controls for opening and closing the jaws, and may include an actuator for sending current through the first and second heating elements. The first and second heating elements may be electrically connected in series, and the first heating element may be bifurcated such that it conducts about one half of the current as the second heating element. A force-limiting mechanism provided either within the control handle, in the elongated shaft, or at the jaws limits the pressure applied to the tissue by the jaws to ensure that the tissue is severed and the ends effectively welded within a short amount of time.

21 Claims, 23 Drawing Sheets

(51) Int. Cl.

| | | |
|---|---|---|
| A61B 17/34 | (2006.01) | |
| A61B 17/29 | (2006.01) | |
| A61B 18/14 | (2006.01) | |
| A61B 17/00 | (2006.01) | |
| A61B 19/00 | (2006.01) | |

(52) U.S. Cl.
CPC ... *A61B18/1445* (2013.01); *A61B 2017/00353* (2013.01); *A61B 2017/00084* (2013.01); *A61B 2017/00504* (2013.01); *A61B 17/29* (2013.01); *A61B 2017/2945* (2013.01); *A61B 2018/1432* (2013.01); *A61B 19/30* (2013.01); *A61B 2017/2936* (2013.01)
USPC .......................................................... 606/29

(56) References Cited

U.S. PATENT DOCUMENTS

| | | | |
|---|---|---|---|
| 4,071,028 A | 1/1978 | Perkins | |
| 4,128,099 A | 12/1978 | Bauer | |
| 4,281,646 A | 8/1981 | Kinoshita | |
| 4,418,692 A | 12/1983 | Guay | |
| 4,468,217 A | 8/1984 | Kuzmick et al. | |
| 4,759,362 A | 7/1988 | Taniguchi | |
| 4,767,519 A | 8/1988 | de Nora | |
| 4,801,015 A | 1/1989 | Lubock et al. | |
| 4,884,559 A | 12/1989 | Collins | |
| 5,009,661 A | 4/1991 | Michelson | |
| 5,052,402 A | 10/1991 | Bencini | |
| 5,098,430 A | 3/1992 | Fleenor | |
| 5,108,474 A | 4/1992 | Riedy et al. | |
| 5,147,356 A | 9/1992 | Bhatta | |
| 5,151,102 A | 9/1992 | Kamiyama et al. | |
| 5,154,709 A | 10/1992 | Johnson | |
| 5,156,613 A | 10/1992 | Sawyer | |
| 5,160,334 A | 11/1992 | Billings | |
| 5,217,460 A | 6/1993 | Knoepfler | |
| 5,258,006 A | 11/1993 | Rydell et al. | |
| 5,282,799 A | 2/1994 | Rydell | |
| 5,290,278 A | 3/1994 | Anderson | |
| 5,300,065 A | 4/1994 | Anderson | |
| 5,312,426 A | 5/1994 | Segawa et al. | |
| 5,314,424 A | 5/1994 | Nicholas | |
| 5,318,040 A | 6/1994 | Kensey et al. | |
| 5,336,221 A | 8/1994 | Anderson | |
| 5,342,381 A | 8/1994 | Tidemand | |
| 5,352,222 A | 10/1994 | Rydell | |
| 5,356,408 A | 10/1994 | Rydell | |
| 5,361,583 A | 11/1994 | Huitema | |
| 5,364,395 A | 11/1994 | West, Jr. | |
| 5,383,888 A | 1/1995 | Zvenyatsky et al. | |
| 5,405,344 A | 4/1995 | Williamson et al. | |
| 5,443,463 A | 8/1995 | Stern et al. | |
| 5,445,638 A | 8/1995 | Rydell et al. | |
| 5,451,222 A | 9/1995 | De Maagd et al. | |
| 5,453,599 A | 9/1995 | Hall, Jr. | |
| 5,462,546 A | 10/1995 | Rydell | |
| 5,472,442 A | 12/1995 | Klicek | |
| 5,496,317 A | 3/1996 | Goble et al. | |
| 5,507,744 A | 4/1996 | Tay et al. | |
| 5,507,773 A | 4/1996 | Huitema et al. | |
| 5,509,922 A | 4/1996 | Aranyi et al. | |
| 5,514,134 A | 5/1996 | Rydell et al. | |
| 5,562,503 A | 10/1996 | Ellman | |
| 5,599,350 A | 2/1997 | Schulze et al. | |
| 5,624,452 A | 4/1997 | Yates | |
| 5,647,871 A | 7/1997 | Levine et al. | |
| 5,669,934 A | 9/1997 | Sawyer | |
| 5,674,219 A | 10/1997 | Monson et al. | |
| 5,683,412 A | 11/1997 | Scarfone | |
| 5,709,675 A | 1/1998 | Williams | |
| 5,709,680 A | 1/1998 | Yates et al. | |
| 5,716,366 A | 2/1998 | Yates | |
| 5,722,962 A | 3/1998 | Garcia | |
| 5,741,285 A | 4/1998 | McBrayer et al. | |
| 5,752,973 A | 5/1998 | Kieturakis | |
| 5,755,717 A | 5/1998 | Yates et al. | |
| 5,766,134 A | 6/1998 | Lisak et al. | |
| 5,766,166 A | 6/1998 | Hooven | |
| 5,776,130 A | 7/1998 | Buysse et al. | |
| 5,807,393 A | 9/1998 | Williamson, IV et al. | |
| 5,810,810 A | 9/1998 | Tay et al. | |
| 5,810,811 A * | 9/1998 | Yates et al. | 606/50 |
| 5,827,271 A | 10/1998 | Buysse et al. | |
| 5,833,690 A | 11/1998 | Yates et al. | |
| 5,843,017 A | 12/1998 | Yoon | |
| 5,849,011 A | 12/1998 | Jones | |
| 5,853,410 A | 12/1998 | Greff et al. | |
| 5,860,975 A | 1/1999 | Goble et al. | |
| 5,871,496 A | 2/1999 | Ginn et al. | |
| 5,891,141 A | 4/1999 | Rydell | |
| 5,906,630 A | 5/1999 | Anderhub et al. | |
| 5,908,420 A | 6/1999 | Parins et al. | |
| 5,911,719 A | 6/1999 | Eggers | |
| 5,944,718 A | 8/1999 | Austin et al. | |
| 5,947,984 A | 9/1999 | Whipple | |
| 5,954,686 A | 9/1999 | Garito | |
| 5,997,533 A | 12/1999 | Kuhns | |
| 6,004,320 A | 12/1999 | Casscells et al. | |
| 6,022,313 A | 2/2000 | Ginn et al. | |
| 6,024,741 A | 2/2000 | Williamson, IV et al. | |
| 6,027,501 A | 2/2000 | Goble et al. | |
| 6,033,424 A | 3/2000 | Ouchi | |
| 6,039,733 A | 3/2000 | Buysse et al. | |
| 6,059,781 A | 5/2000 | Yamanashi et al. | |
| 6,066,151 A | 5/2000 | Miyawaki | |
| 6,074,389 A | 6/2000 | Levine et al. | |
| 6,110,190 A | 8/2000 | Ginn et al. | |
| 6,113,596 A | 9/2000 | Hooven | |
| 6,174,309 B1 | 1/2001 | Wrublewski et al. | |
| 6,179,837 B1 | 1/2001 | Hooven | |
| 6,190,386 B1 | 2/2001 | Rydell | |
| 6,206,876 B1 | 3/2001 | Levine et al. | |
| 6,254,623 B1 | 7/2001 | Haibel, Jr. et al. | |
| 6,267,761 B1 | 7/2001 | Ryan | |
| 6,270,497 B1 | 8/2001 | Sekino | |
| 6,273,887 B1 | 8/2001 | Yamauchi et al. | |
| 6,352,503 B1 | 3/2002 | Matsui et al. | |
| 6,352,532 B1 | 3/2002 | Kramer et al. | |
| 6,391,029 B1 | 5/2002 | Hooven et al. | |
| 6,406,454 B1 | 6/2002 | Hajianpour | |
| 6,432,105 B1 | 8/2002 | Ellman et al. | |
| 6,458,122 B1 | 10/2002 | Pozzato | |
| 6,464,701 B1 | 10/2002 | Hooven et al. | |
| 6,478,794 B1 | 11/2002 | Trapp et al. | |
| 6,517,536 B2 | 2/2003 | Hooven et al. | |
| 6,524,307 B1 | 2/2003 | Palmerton et al. | |
| 6,527,771 B1 | 3/2003 | Weadock et al. | |
| 6,544,210 B1 | 4/2003 | Trudel et al. | |
| 6,551,313 B1 | 4/2003 | Levin | |
| 6,576,033 B1 | 6/2003 | Booth | |
| 6,582,451 B1 | 6/2003 | Marucci et al. | |
| 6,582,582 B2 | 6/2003 | Becking | |
| 6,602,252 B2 * | 8/2003 | Mollenauer | 606/46 |
| 6,613,069 B2 | 9/2003 | Boyd et al. | |
| 6,626,901 B1 | 9/2003 | Treat et al. | |
| 6,652,514 B2 | 11/2003 | Ellman | |
| 6,656,177 B2 | 12/2003 | Truckai et al. | |
| 6,663,610 B1 | 12/2003 | Thompson et al. | |
| 6,682,528 B2 | 1/2004 | Frazier et al. | |
| 6,685,665 B2 | 2/2004 | Booth et al. | |
| 6,695,837 B2 | 2/2004 | Howell | |
| 6,746,504 B2 | 6/2004 | Booth | |
| 6,770,072 B1 | 8/2004 | Truckai et al. | |
| 6,773,409 B2 | 8/2004 | Truckai et al. | |
| 6,802,843 B2 | 10/2004 | Truckai et al. | |
| 6,821,273 B2 | 11/2004 | Mollenauer | |
| 6,830,569 B2 | 12/2004 | Thompson | |
| 6,860,880 B2 | 3/2005 | Treat et al. | |
| 6,908,463 B2 | 6/2005 | Treat et al. | |
| 6,958,070 B2 | 10/2005 | Witt et al. | |
| 6,966,907 B2 | 11/2005 | Goble | |
| 6,966,909 B2 | 11/2005 | Marshall et al. | |
| 6,994,707 B2 | 2/2006 | Ellman | |

(56) References Cited

U.S. PATENT DOCUMENTS

| | | | |
|---|---|---|---|
| 7,033,356 B2 | 4/2006 | Latterell et al. | |
| 7,083,620 B2 | 8/2006 | Jahns et al. | |
| 7,094,231 B1 | 8/2006 | Ellman | |
| 7,112,199 B2 | 9/2006 | Cosmescu | |
| 7,147,637 B2 | 12/2006 | Goble | |
| 7,204,835 B2 | 4/2007 | Latterell et al. | |
| 7,211,080 B2 | 5/2007 | Treat et al. | |
| 7,306,599 B2 | 12/2007 | Karasawa et al. | |
| 7,316,683 B2 | 1/2008 | Kasahara et al. | |
| 7,326,202 B2 | 2/2008 | McGaffigan | |
| 7,364,577 B2 | 4/2008 | Wham | |
| 7,367,976 B2 | 5/2008 | Lawes et al. | |
| 7,396,356 B2 | 7/2008 | Mollenauer | |
| 7,513,896 B2 | 4/2009 | Orszulak | |
| 7,632,270 B2 | 12/2009 | Livneh | |
| 7,645,289 B2 | 1/2010 | Bayer | |
| 7,699,861 B2 | 4/2010 | Bayer | |
| 7,887,558 B2 | 2/2011 | Lin et al. | |
| 7,918,845 B2 | 4/2011 | Saadat et al. | |
| 7,918,848 B2 | 4/2011 | Lau et al. | |
| 8,197,472 B2 * | 6/2012 | Lau et al. | 606/29 |
| 8,221,306 B2 | 7/2012 | Okada et al. | |
| 8,251,989 B1 | 8/2012 | Newton et al. | |
| 8,257,352 B2 | 9/2012 | Lawes et al. | |
| 8,425,508 B2 | 4/2013 | Kasahara et al. | |
| 8,623,003 B2 | 1/2014 | Lau et al. | |
| 8,657,818 B2 | 2/2014 | Lin | |
| 2002/0019631 A1 | 2/2002 | Kidder et al. | |
| 2002/0058938 A1 | 5/2002 | Cosmescu | |
| 2002/0128603 A1 | 9/2002 | Booth et al. | |
| 2003/0014052 A1 | 1/2003 | Buysse et al. | |
| 2003/0060816 A1 | 3/2003 | Iida | |
| 2003/0125734 A1 | 7/2003 | Mollenauer | |
| 2003/0144652 A1 | 7/2003 | Baker | |
| 2003/0144660 A1 | 7/2003 | Mollenauer | |
| 2003/0163123 A1 | 8/2003 | Goble et al. | |
| 2003/0171747 A1 | 9/2003 | Kanehira et al. | |
| 2003/0187429 A1 | 10/2003 | Karasawa et al. | |
| 2004/0054365 A1 | 3/2004 | Goble | |
| 2004/0064151 A1 | 4/2004 | Mollenauer | |
| 2004/0078035 A1 * | 4/2004 | Kanehira et al. | 606/28 |
| 2004/0133228 A1 | 7/2004 | Bayer | |
| 2004/0176756 A1 | 9/2004 | McGaffigan | |
| 2004/0204725 A1 | 10/2004 | Bayer | |
| 2004/0260279 A1 | 12/2004 | Goble et al. | |
| 2005/0033278 A1 | 2/2005 | McClurken et al. | |
| 2005/0049633 A1 | 3/2005 | Watanabe | |
| 2005/0072827 A1 | 4/2005 | Mollenauer | |
| 2005/0113828 A1 | 5/2005 | Shields et al. | |
| 2005/0171533 A1 | 8/2005 | Latterell et al. | |
| 2006/0074444 A1 | 4/2006 | Lin et al. | |
| 2006/0211916 A1 | 9/2006 | Kasahara et al. | |
| 2006/0217697 A1 | 9/2006 | Lau et al. | |
| 2006/0217706 A1 | 9/2006 | Lau et al. | |
| 2006/0235379 A1 | 10/2006 | McClurken et al. | |
| 2007/0078456 A1 | 4/2007 | Dumbauld et al. | |
| 2007/0149993 A1 | 6/2007 | Kasahara et al. | |
| 2007/0213749 A1 | 9/2007 | Kogasaka et al. | |
| 2007/0260242 A1 * | 11/2007 | Dycus et al. | 606/51 |
| 2007/0293856 A1 | 12/2007 | Paul | |
| 2007/0293858 A1 | 12/2007 | Fischer | |
| 2008/0015567 A1 | 1/2008 | Kimura | |
| 2008/0015575 A1 | 1/2008 | Odom | |
| 2008/0154091 A1 | 6/2008 | Dejima et al. | |
| 2008/0306335 A1 | 12/2008 | Lau et al. | |
| 2009/0024121 A1 | 1/2009 | Kasahara et al. | |
| 2009/0118730 A1 | 5/2009 | Mollenauer | |
| 2009/0299367 A1 | 12/2009 | Ginnebaugh et al. | |
| 2010/0048992 A1 | 2/2010 | Okada et al. | |
| 2010/0292533 A1 | 11/2010 | Kasahara et al. | |
| 2011/0046439 A1 | 2/2011 | Pamnani et al. | |
| 2011/0046624 A1 | 2/2011 | Lin | |
| 2011/0257643 A1 | 10/2011 | Lau | |
| 2011/0288369 A1 | 11/2011 | Ginnebaugh | |
| 2011/0288546 A1 | 11/2011 | Abbott | |
| 2012/0283720 A1 | 11/2012 | Newton et al. | |
| 2012/0316550 A1 | 12/2012 | Lau et al. | |
| 2013/0018373 A1 | 1/2013 | Lau et al. | |

FOREIGN PATENT DOCUMENTS

| | | |
|---|---|---|
| JP | 05-23-2000 A | 5/2000 |
| JP | 2003-144451 A | 5/2003 |
| JP | 2005-058553 A | 3/2005 |
| WO | 0047124 A1 | 8/2000 |
| WO | 02080794 A1 | 10/2002 |
| WO | 03057058 A1 | 7/2003 |

OTHER PUBLICATIONS

PCT International Preliminary Report on Patentability, PCT/US2006/010569, mailed Oct. 4, 2007, 10 pages.

PCT International Search Report, PCT/US2006/010568, mailed Jul. 24, 2006, 3 pages.

PCT International Preliminary Report on Patentability, PCT/US2006/010568, mailed Oct. 4, 2007, 7 pages.

European Examination Report, EP 06739388.4, mailed Sep. 17, 2008, 7 pages.

* cited by examiner

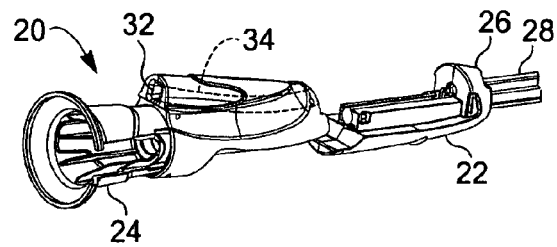
Fig.1A
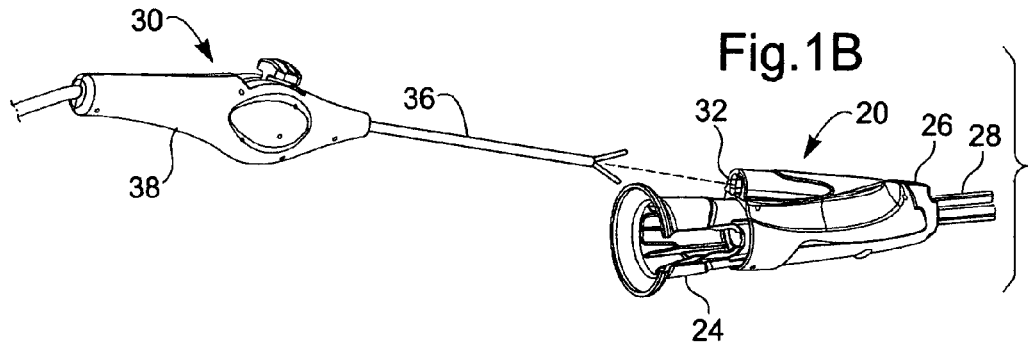
Fig.1B
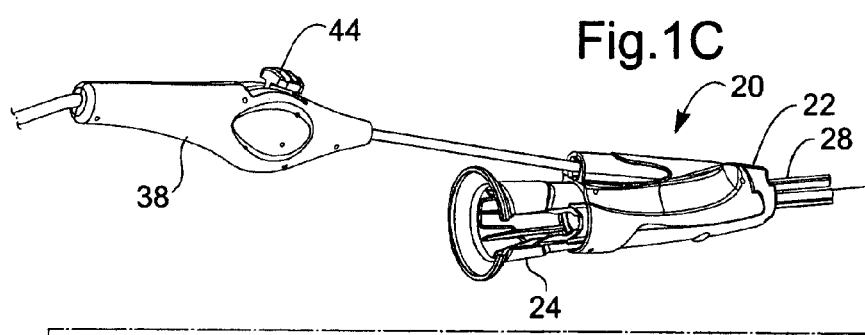
Fig.1C
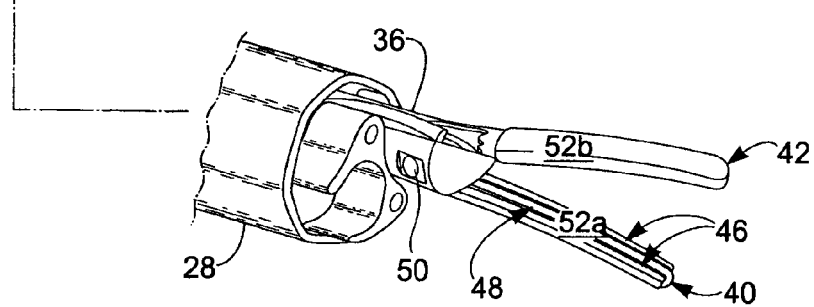

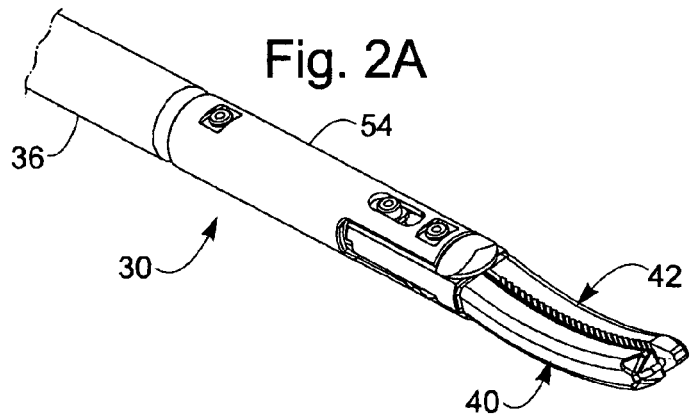
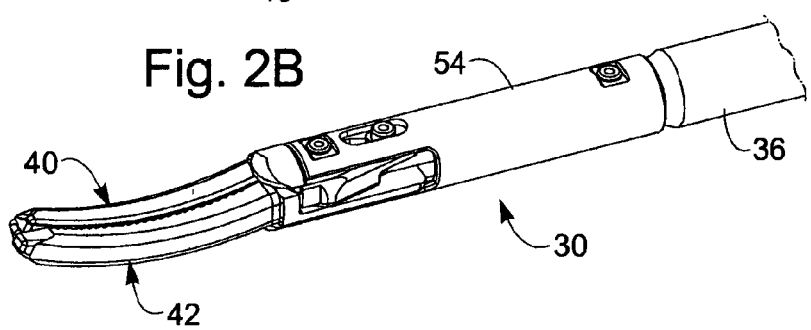
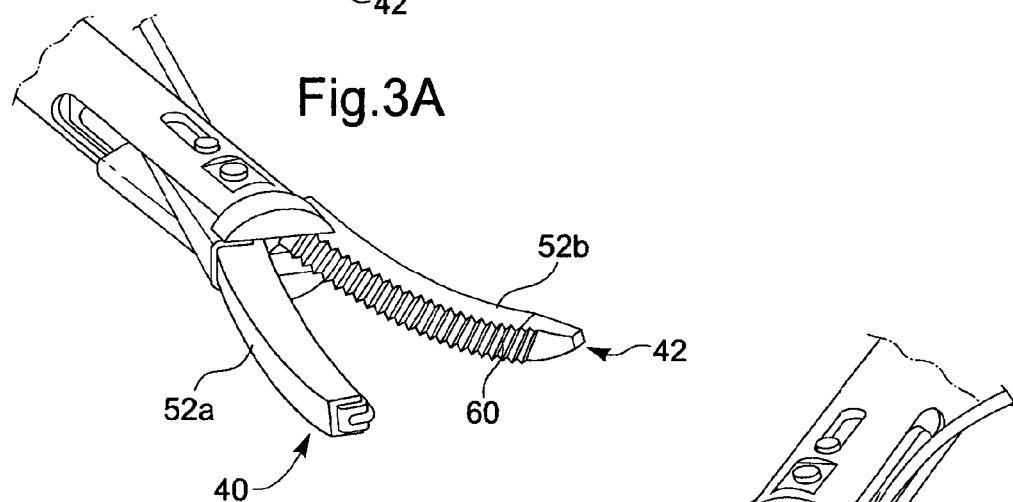
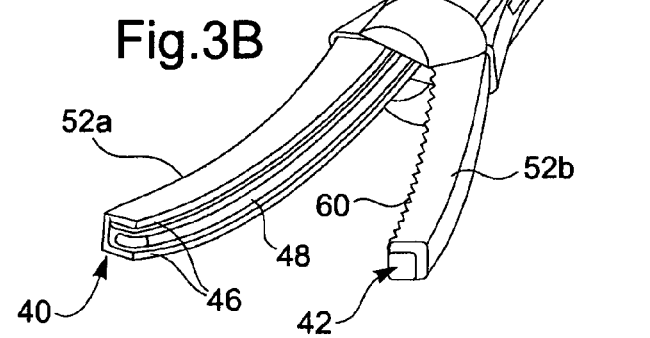

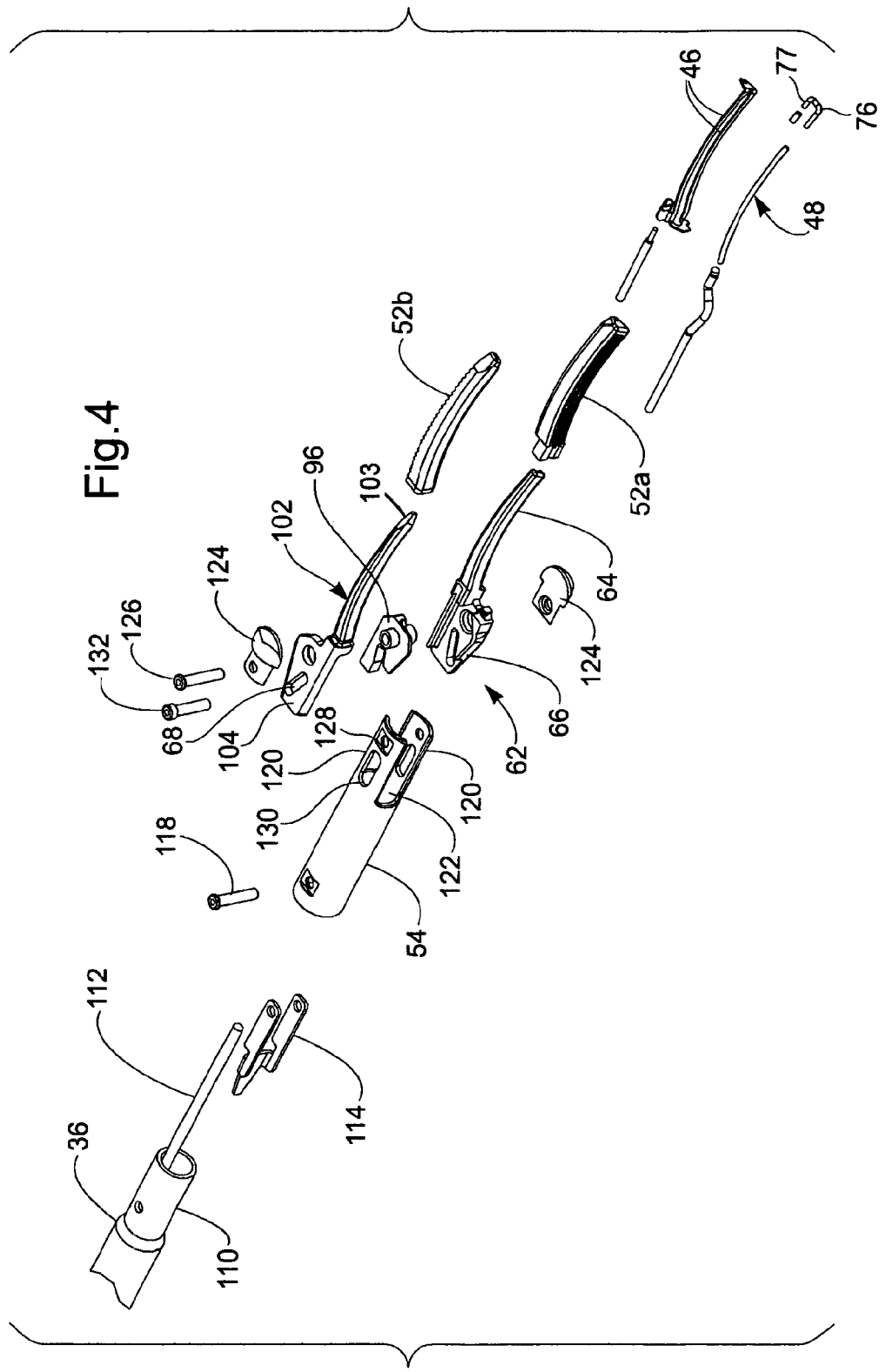

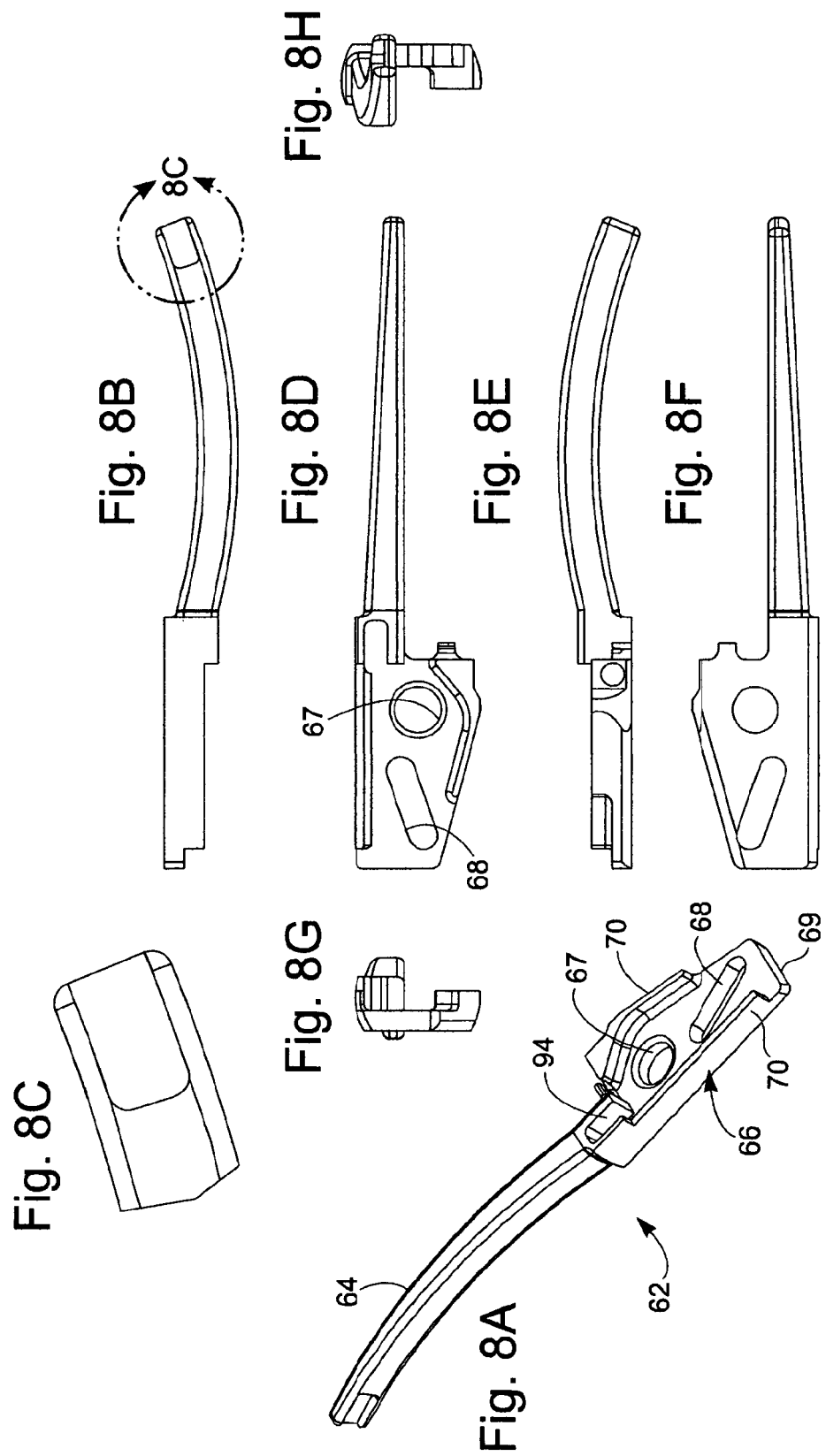

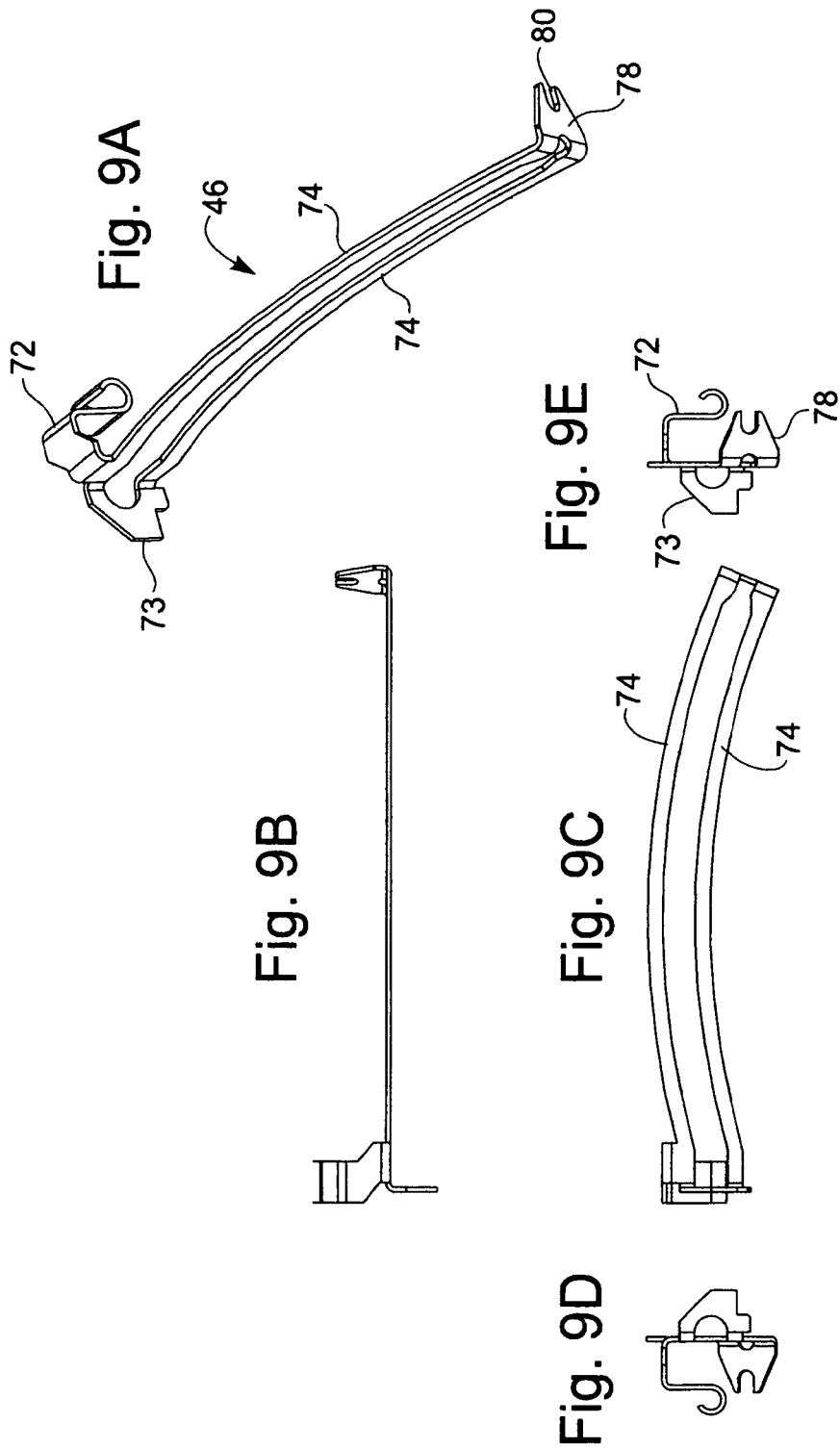

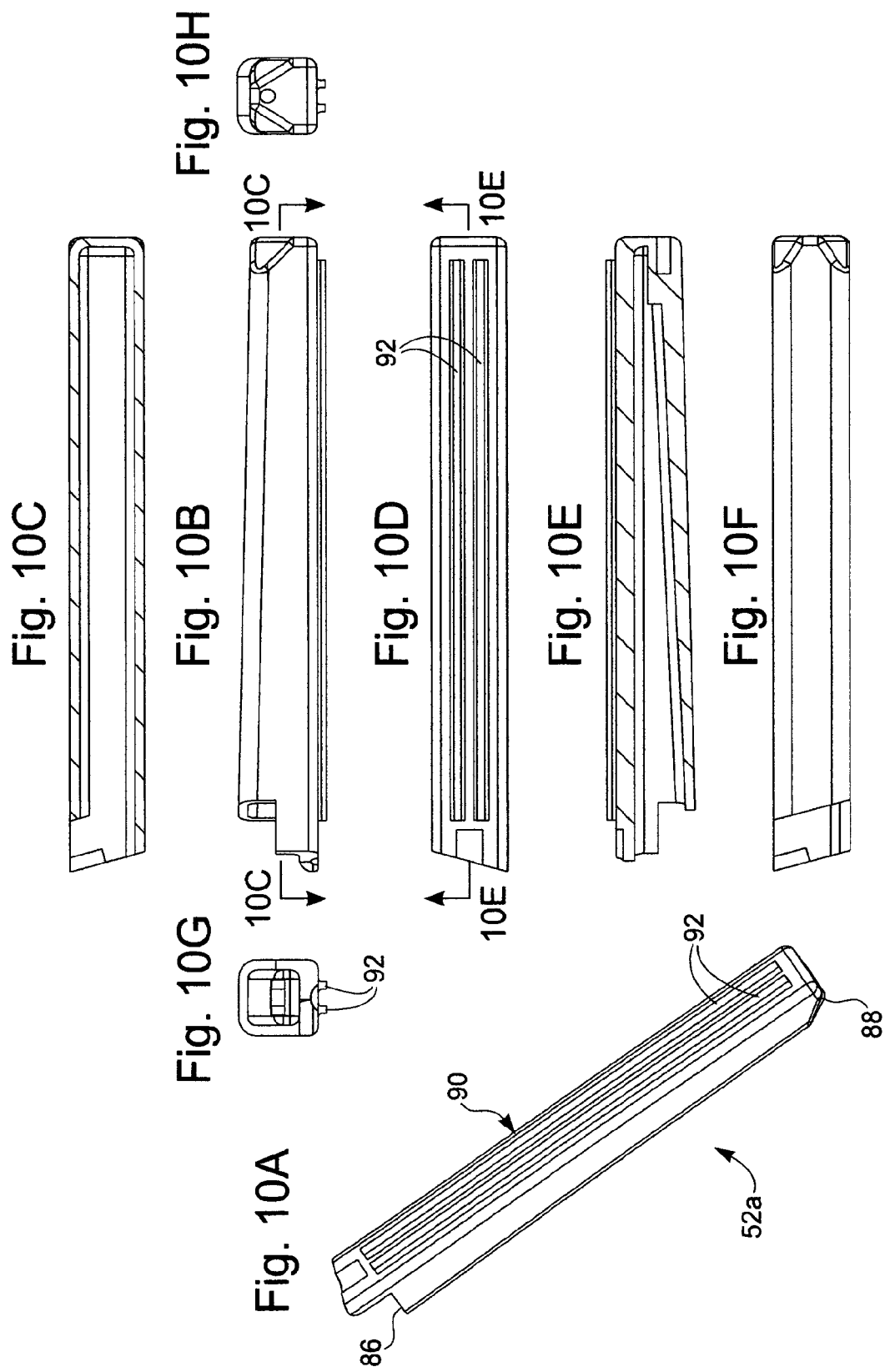

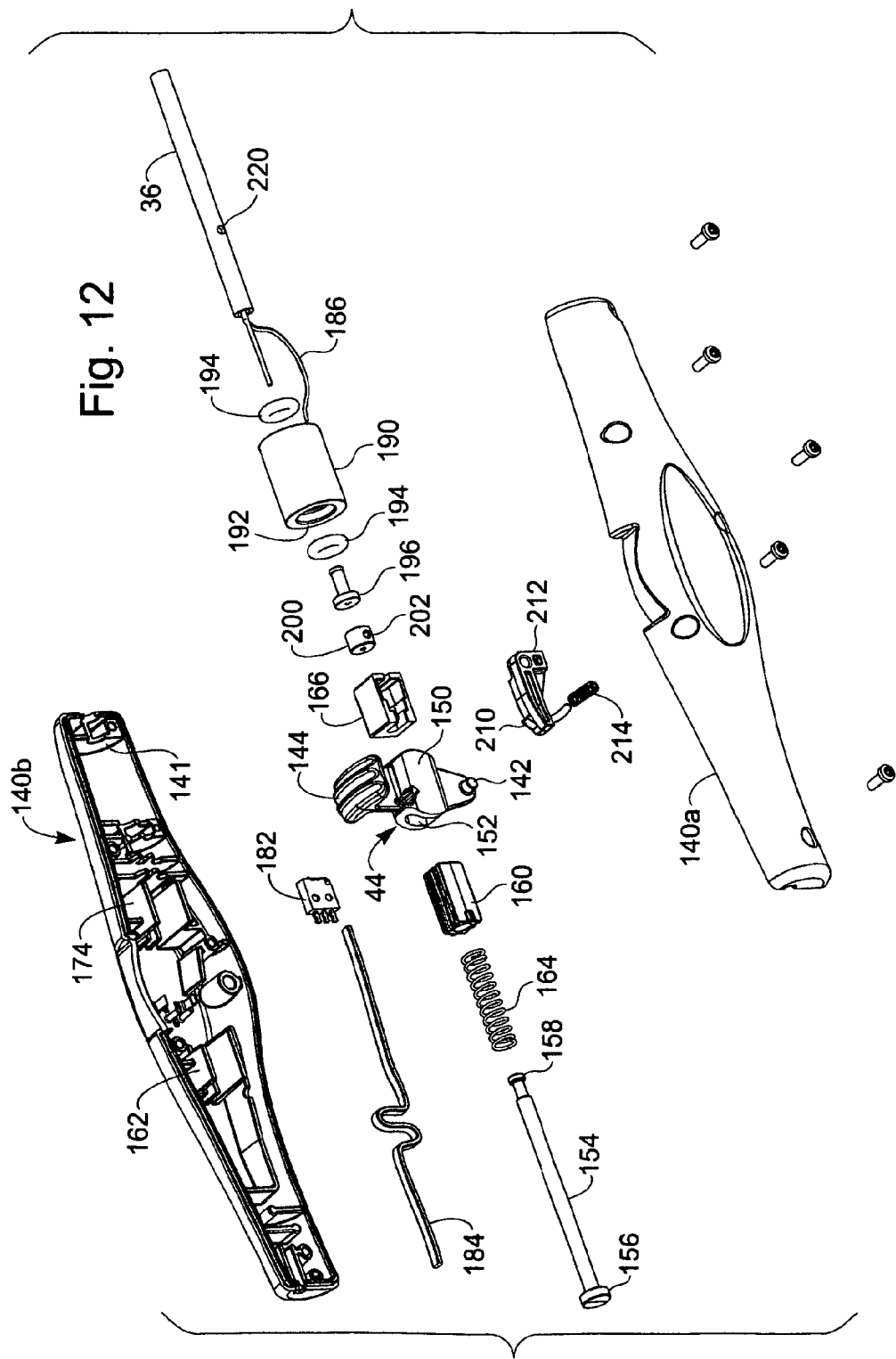

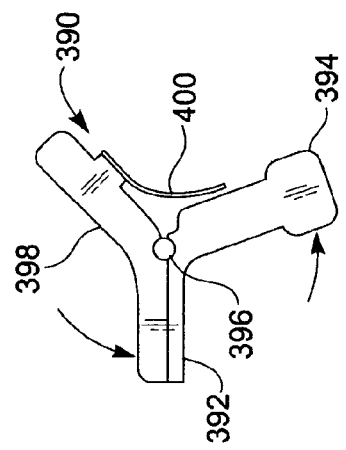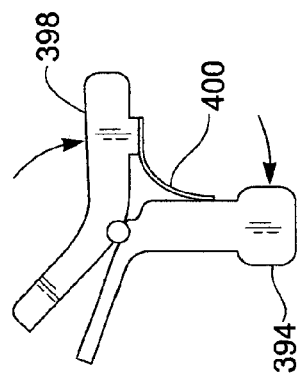
Fig. 17A  Fig. 17B
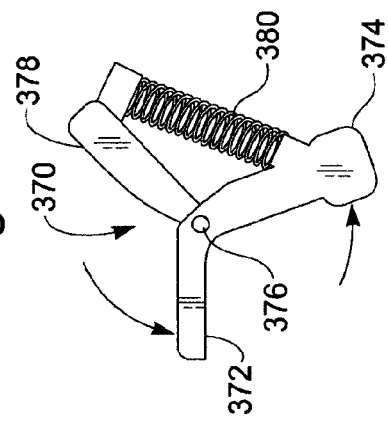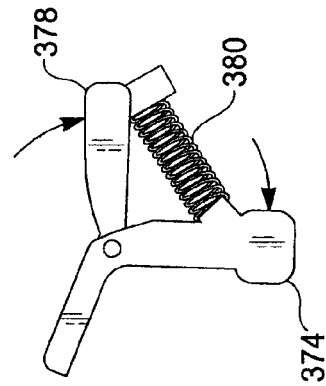
Fig. 16A  Fig. 16B
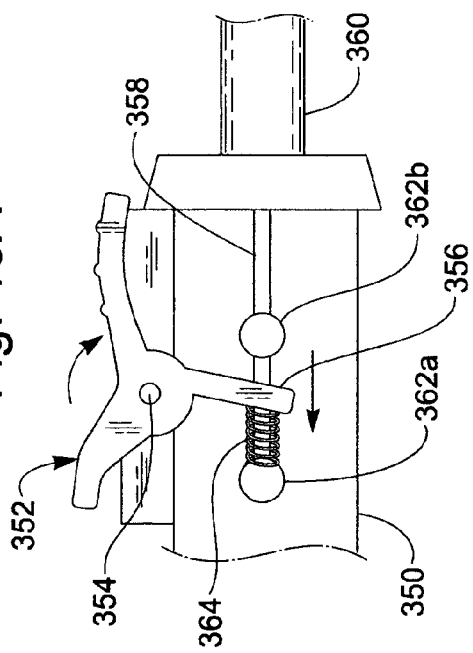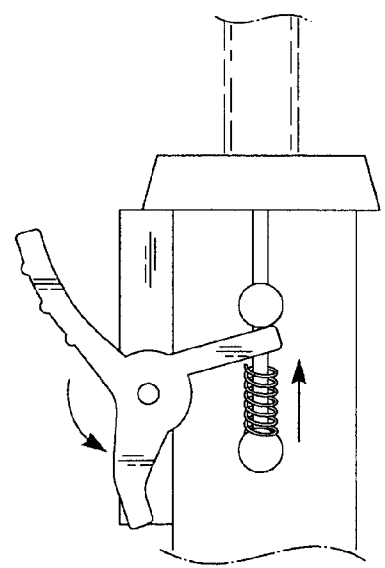
Fig. 15A  Fig. 15B

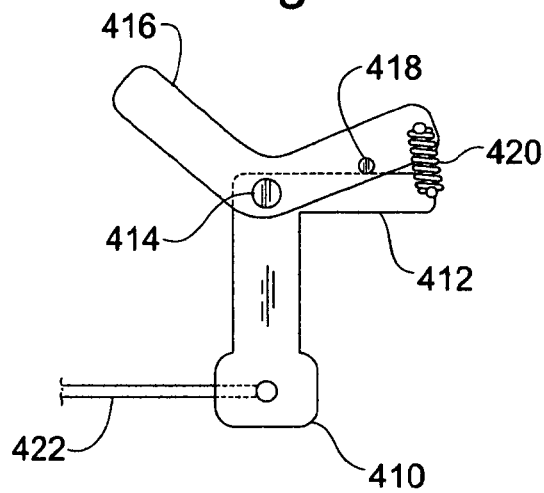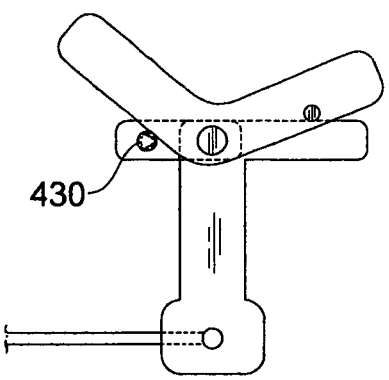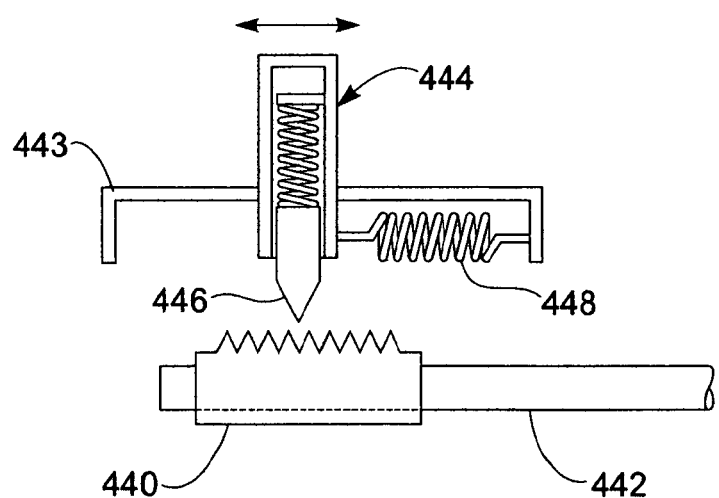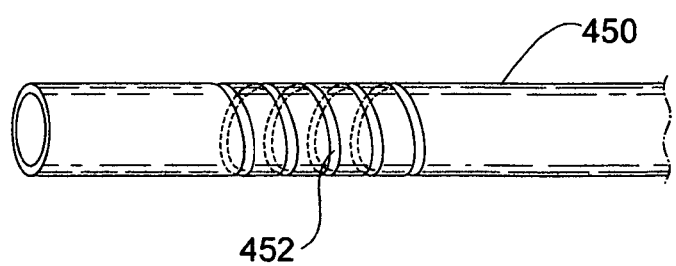

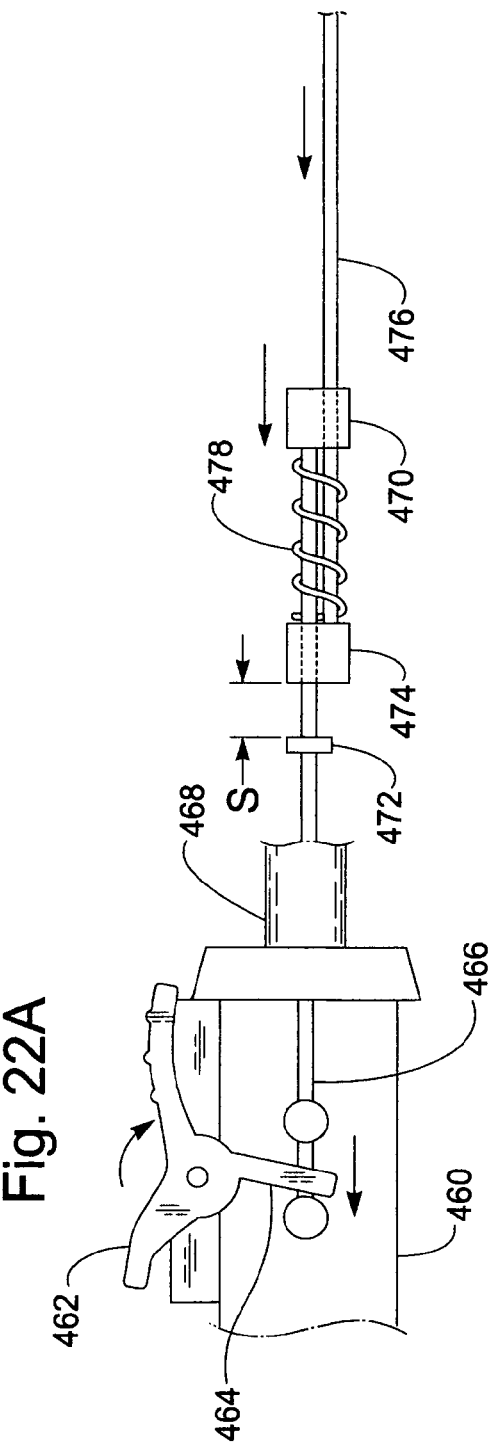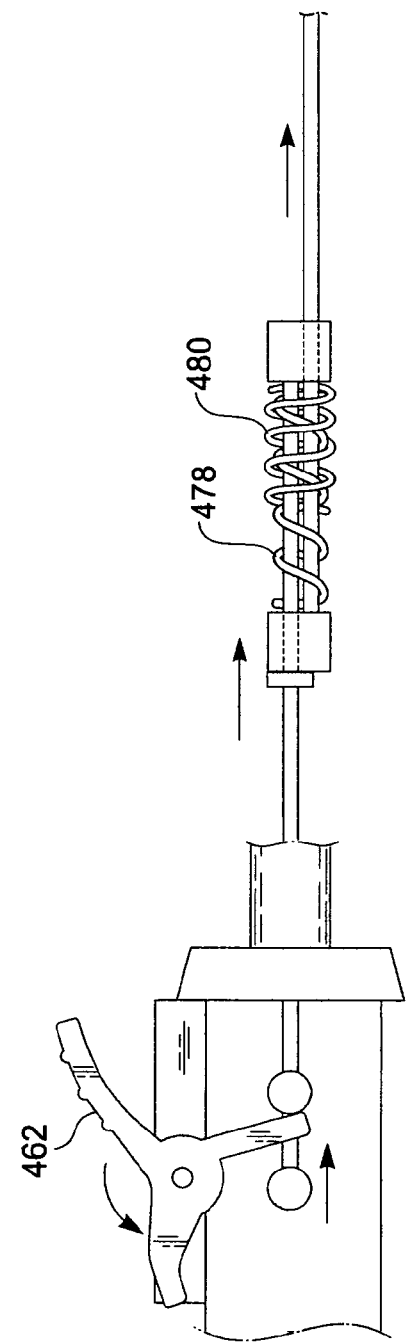

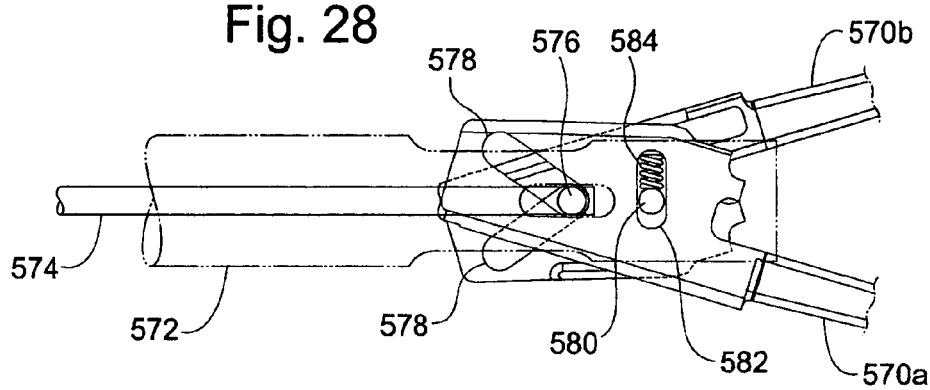
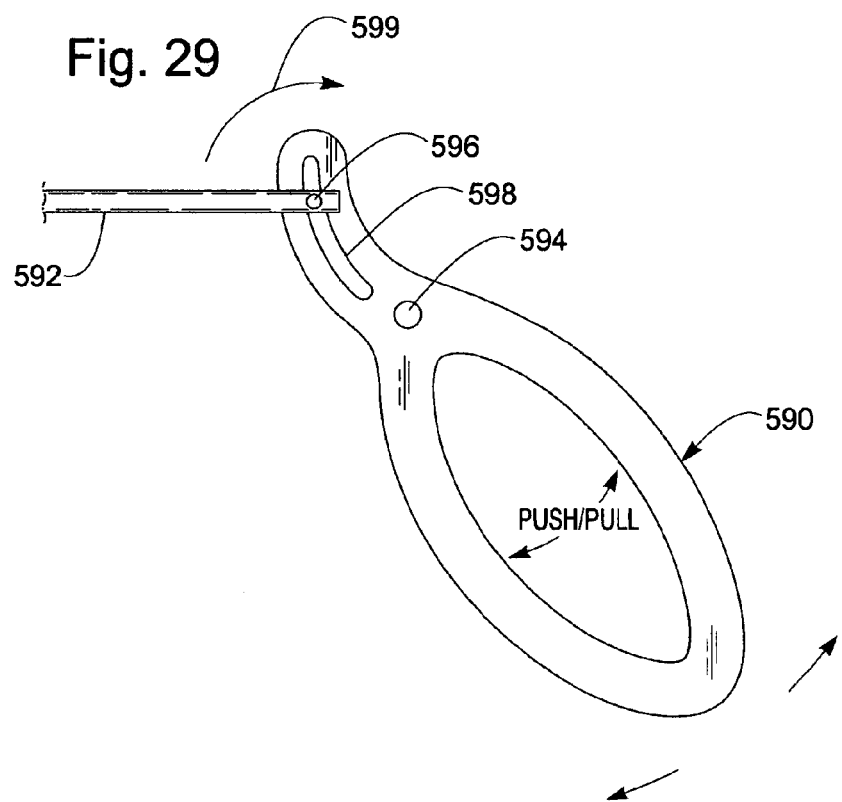

APPARATUS AND METHOD FOR REGULATING TISSUE WELDER JAWS

RELATED APPLICATIONS

This application is a continuation of U.S. patent application Ser. No. 13/549,367, filed on Jul. 13, 2012, Now issued as U.S. Pat. No. 8,623,003, which is a continuation of U.S. patent application Ser. No. 13/047,778, filed on Mar. 14, 2011, now abandoned, which is a continuation of U.S. patent application Ser. No. 11/090,330, filed Mar. 25, 2005, Now issued as U.S. Pat. No. 7,918,848. The entire disclosures of all of the above applications are expressly incorporated by reference herein.

The present application relates to application Ser. No. 11/090,750, filed Mar. 25, 2005, now U.S. Pat. No. 8,197,472, the entire disclosure of which is expressly incorporated by reference herein.

FIELD OF THE INVENTION

The present invention relates to surgical devices and methods for severing and sealing blood vessels and, in particular, to an endoscopic tissue welder.

BACKGROUND OF THE INVENTION

Endoscopic harvesting of vessels is well known in the surgical field and has been the subject of a great deal of recent technological advancement. Typically, the harvested vessel is used for bypass or as a shunt around an artery that has diminished flow from stenosis or other anomaly, such as a Coronary Artery Bypass Grafting (CABG) procedure. Often in CABG, a saphenous vein from the patient's leg is harvested for subsequent use in the surgery. Other vessels, such as the radial artery, can also be harvested and used in this manner. Vessel harvesting involves liberating the vessel from surrounding tissue and transecting smaller side branches, cauterizing, tying or ligating the vessel at a proximal site and a distal site, and then transecting the vessel at both sites before it is removed from the body.

Known endoscopic methods and devices for performing vessel harvesting are discussed in detail in U.S. Pat. Nos. 6,176,895 to Chin, et al., Re 36,043 to Knighton, U.S. Pat. Nos. 6,406,425 to Chin, et al., and 6,471,638 to Chang, et al., all of which are expressly incorporated herein by reference. Furthermore, various devices and methods disclosed in U.S. Pat. Nos. 5,895,353 to Lunsford, et al., and 6,162,173 to Chin, et al., and pending patent application Ser. No. 10/602,490 entitled "Apparatus and Method for Integrated Vessel Ligator and Transector" are also expressly incorporated herein by reference. Also, commercial vessel harvesting systems sold under the tradename VASOVIEW® Uniport Plus and VASOVIEW® 5 are available from Guidant Corporation of Santa Clara, Calif.

Numerous instruments are known which coagulate, seal, join, or cut tissue, and which are suitable, for example, for severing a target vessel from surrounding side branches and securing the separated ends to stanch bleeding. Such devices typically comprise a pair of tweezers, jaws or forceps that grasp onto and hold tissue therebetween. The devices may operate with a heating element in contact with the tissue, with an ultrasonic heater that employs frictional heating of the tissue, or with a mono- or bi-polar electrode heating system that passes current through the tissue such that the tissue is heated by virtue of its own electrical resistance. The devices heat the tissue to temperatures such that the tissue is either "cut" or "sealed", as follows. When tissue is heated in excess of 100° Celsius, the tissue disposed between the tweezers, jaws or forceps will be broken down and is thus, "cut". However, when the tissue is heated to temperatures between 50° to 90° Celsius, the tissue will instead simply "seal" or "weld" to adjacent tissue. In the context of the present application, the term "tissue welding" refers to procedures that cause otherwise separated tissue to be sealed, coagulated, fused, welded or otherwise joined together. Numerous devices employing the same general principle of controlled application of a combination of heat and pressure can be used to join or "weld" adjacent tissues to produce a junction of tissues or an anastomosis of tubular tissues.

Monopolar and bipolar probes, forceps or scissors use high frequency electrical current that passes through the tissue to be coagulated. The current passing through the tissue causes the tissue to be heated, resulting in coagulation of tissue proteins. In the monopolar variety of these instruments, the current leaves the electrode and after passing through the tissue, returns to the generator by means of a "ground plate" which is attached or connected to a distant part of the patient's body. In a bipolar version of such an electro-surgical instrument, the electric current passes between two electrodes with the tissue being placed or held between the two electrodes as in the "Kleppinger bipolar forceps" used for occlusion of Fallopian tubes. There are many examples of such monopolar and bipolar instruments commercially available today from companies including Valley Lab, Cabot, Meditron, Wolf, Storz and others worldwide.

A new development in this area is the "Tripolar" instrument marketed by Cabot and Circon-ACMI which incorporates a mechanical cutting element in addition to monopolar coagulating electrodes. A similar combined sealing and mechanical cutting device may also be known as a tissue "bisector," which merges the terms bipolar cautery and dissector. One tissue bisector is packaged for sale as an element of the VASOVIEW® Uniport Plus and VASOVIEW® 5 vessel harvesting systems by Guidant Corporation of Santa Clara, Calif.

In ultrasonic tissue heaters, a very high frequency (ultrasonic) vibrating element or rod is held in contact with the tissue. The rapid vibrations generate heat causing the proteins in the tissue to become coagulated.

Conductive tissue welders usually include jaws that clamp tissue therebetween, one or both of which are resistively heated. In this type of instrument, no electrical current passes through the tissue, as is the case for monopolar or bipolar cautery. Some tissue welders also perform a severing function without a mechanical knife. For example, the Thermal Ligating Shears made by Starion Instruments of Saratoga, Calif. is a, hand activated instrument that utilizes thermal welding to simultaneously seal and divide soft tissue during laparoscopic general surgery procedures. The Starion device uses a heating element at the tip of one of a pair of facing jaws combined with pressure to denature the protein molecules within the tissue. The denatured proteins bond together, forming an amorphous mass of protein, and fusing tissue layers together. The procedure can be used to fuse vessels closed. More highly focused heat may be applied in the center of the tissue within the jaws of the instrument, causing the tissue or vessel to divide, thus resulting in two sealed ends. A description of the Starion device is provided at www.starioninstruments.com.

Despite accepted means for severing and securing vessels, such as in a vessel harvesting procedure, there remains a need for an improved device that increases the operating efficiency of the device and ensures the least amount of trauma to surrounding tissue while simultaneously providing repeatable secure sealing of the severed vessel ends.

SUMMARY OF THE INVENTION

The present invention provides designs of tissue severing/sealing devices that control the pressure applied to tissue between the distal jaws to avoid crushing an improved the severing and welding process.

In one embodiment, the present invention includes a surgical apparatus for welding and severing tissue comprising first and second relatively movable elongated jaws having facing surfaces. The first and second relatively movable jaws attach to a distal end of an elongated shaft, and at least one heating element is provided on the facing surface of one of the first or second jaws. A control handle connects to the elongated shaft, and a control actuator alternately separates and brings together the facing surfaces of the elongated jaws. Finally, a force-limiting mechanism interposed between the control actuator and the jaws regulates the magnitude of closing force of the jaws to between about 1-3 lbs (0.45-1.36 kg) to ensure the heating element effectively welds and severs tissue held within the facing surfaces of the closed elongated jaws. In an alternative arrangement, the force-limiting mechanism regulates the magnitude of closing force of the jaws so that the heating element effectively welds and severs tissue held within the facing surfaces of the closed elongated jaws within a time frame of 5 seconds or less. In a preferred embodiment, a second heating element is provided on the facing surface of one of the first or second jaws, wherein the first heating element is adapted to weld tissue and the second heating element is adapted to sever tissue.

Desirably, a control rod extends from the control handle to the distal end of the elongated shaft and connects to translate movement of the control actuator into movement of the jaws. In one configuration, the force-limiting mechanism comprising a spring mounted coaxially on the control rod. The spring may be located within the elongated shaft, and may even be formed by a portion of the control rod such as a helical laser cut within a tubular control rod. In addition, a second spring may mount coaxially on the control rod and be arranged such that deformation of the first and second springs does not occur simultaneously upon closing of the jaws. In a second configuration, the force-limiting mechanism comprises a spring located within the control handle. For example, the control actuator may comprise a toggle journalled to pivot in two directions and accordingly displace the control rod in opposite directions, wherein the spring is arranged to affect relative movement of the toggle and the control rod in one direction of pivot of the toggle. Alternatively, the force-limiting mechanism includes a ball-detent structure arranged to decouple (or clutch) relative movement of the toggle and the control rod in one direction of pivot of the toggle at a predetermined reaction force transmitted through the control rod from closing of the jaws.

In accordance with an alternative configuration, the force-limiting mechanism comprises an elastic member incorporated within the jaws. For example, the elastic member may be bi-metallic springs adapted to change shape at elevated temperatures. Or, the elastic member may be a compliant layer on at least one of the jaws. In another arrangement, the elastic member comprises a spring positioned between the proximal ends of two jaws which permits the proximal ends to separate at a predetermined force impeding further closing movement of the jaws.

In one embodiment, the jaws are mounted in parallel on the end of the elongated shaft, wherein the apparatus further includes structure for maintaining the parallelism of the jaws during opening and closing thereof.

Another aspect of the invention is a surgical method of severing a target tissue while welding the severed ends. The method first includes providing a surgical apparatus for welding tissue including a pair of jaws having facing surfaces adapted to open and close upon the target tissue, at least one of the jaws including an electrically-resistive heating element on its facing surface. The jaws are closed upon a target tissue, and the magnitude of closing force of the jaws is limited to a value calibrated to ensure the heating element effectively severs and welds tissue held within the facing surfaces of the jaws within a time frame of about 5 seconds or less. The first heating element is energized to form a welded region in the target tissue and sever the target tissue within the welded region. Preferably, the step of limiting the magnitude of closing force of the jaws comprises regulating the magnitude of closing force of the jaws to between about 1-3 lbs (0.45-1.36 kg). In addition, a second resistive heating element for severing tissue may be provided on the facing surface of one of the first or second jaws, the method including electrically energizing the second heating element to sever the target tissue within the welded region.

The method may also include maintaining parallelism between the jaws during the step of closing the jaws upon target tissue. Desirably, the surgical apparatus further includes a control handle having a control actuator for opening and closing the jaws. In one embodiment, the structure between the control actuator and the jaws completely decouples relative movement of the control actuator and the jaws at a predetermined closing force. In this case, the method includes closing the jaws until the predetermined closing force has been reached so that movement of the jaws is decoupled from further movement of the control actuator. Alternatively, the structure between the control actuator and the jaws influences relative movement of the control actuator and the jaws at a predetermined closing force. In the latter instance, the method includes closing the jaws until the predetermined closing force has been reached so that the closing force applied by the jaws on the target tissue remains constant even with further movement of the control actuator.

Another desirable aspect of the present invention is a surgical apparatus for welding tissue comprising an elongated shaft having a means for cauterizing tissue attached to a distal end thereof, the shaft having an internal channel along its length for passage of gas. A control handle connects to the elongated shaft, and a passive filter mounts within the control handle to intercept gas passing in a proximal direction through the channel of the elongated shaft so as to filter the gas before it is released to the interior of the control handle or the environment. The means for cauterizing tissue may comprise a pair of jaws for closing on tissue, and preferably one of the jaws has an electrically-resistive heating element thereon. In a preferred embodiment, the elongated shaft has at least one port formed therein within the control handle open to the internal channel, and wherein the passive filter comprises a hollow permeable member arranged around the elongated shaft at the port. The passive filter may comprise a tubular member sealed at both ends around the elongated shaft and having an enlarged hollow cavity therein adjacent to which the port vents. The apparatus also incorporate means for insufflating a body cavity such that a positive pressure within the body cavity forces gas in a proximal direction through the internal channel of the elongated shaft.

A further alternative aspect of the invention is a surgical apparatus for welding tissue comprising first and second relatively movable elongated jaws having facing surfaces. The relatively movable jaws attach to a distal end of an elongated shaft, and at least one heating element is provided on the facing surface of one of the jaws. A control handle connects to the elongated shaft and a control actuator mounts on the handle for alternately separating and bringing together the facing surfaces of the elongated jaws. A control rod extends from the control handle to the distal end of the elongated shaft and connects to translate movement of the control actuator into movement of the jaws. Finally, an electromotive actuator interposed between the control actuator and the jaws displaces the control rod.

In a still further aspect, the invention includes a surgical apparatus for welding tissue comprising first and second relatively movable elongated jaws having facing surfaces. The relatively movable jaws attach to a distal end of an elongated shaft, and at least one heating element is provided on the facing surface of one of the jaws. A control handle connects to the elongated shaft and a control actuator mounts on the handle for alternately separating and bringing together the facing surfaces of the elongated jaws. Additionally, a compliant layer on one of the elongated jaws deforms upon jaw closing and limits the magnitude of closing force of the jaws. In one configuration, the compliant layer is provided as a middle layer on one of the jaws with a rigid tissue contacting plate to the inside of the jaw that contacts tissue. Upon jaw closing, the compliant middle layer compresses to a greater extent at its proximal end such that the rigid tissue contacting plate floats on the jaw and helps even out clamping pressure on the tissue. In an alternative configuration, the compliant layer comprises a tissue contacting surface of one of the jaws, and the opposite jaw includes a heating element that projects inward from that jaw, wherein the compliant layer conforms to the shape of the heating element on the opposite jaw when the jaws are closed.

In a still further aspect of the invention, a surgical apparatus for welding tissue comprises first and second relatively movable elongated jaws having facing surfaces. The relatively movable jaws attach to a distal end of an elongated shaft, and at least one heating element is provided on the facing surface of one of the jaws. A control rod extends from the control handle to the distal end of the elongated shaft and connected to translate movement of the control actuator into movement of the jaws. Finally, a control handle connects to the elongated shaft and a control actuator mounts on the handle for alternately separating and bringing together the facing surfaces of the elongated jaws. The control actuator includes a cam slot that receives a member connected to the control rod, the cam slot being shaped to displace the control rod at a non-linear rate. Preferably, the cam slot is shaped such that as the jaws begin to come together their rate of closure decreases, and as the jaws begin to open their rate of separation increases.

In accordance with a still further aspect of the invention, a surgical apparatus for welding tissue comprises first and second relatively movable elongated jaws having facing surfaces. The relatively movable jaws attach to a distal end of an elongated shaft, and at least one heating element is provided on the facing surface of one of the jaws. A control handle connects to the elongated shaft and a control actuator mounted on the handle alternately separates and brings together the facing surfaces of the elongated jaws. Each of the jaws has a transverse width, and one of the jaws has a transverse width that is at least 20% less than the transverse width of the other jaw.

Another aspect of the invention is a surgical apparatus for welding tissue comprising first and second relatively movable elongated jaws comprising inner jaw members surrounded by tissue-resistant boots, wherein the shape of at least one of the boots on its surface that faces the other jaw is convex. The relatively movable jaws attach to a distal end of an elongated shaft, and at least one heating element is provided on the facing surface of one of the jaws. A control handle connects to the elongated shaft and a control actuator mounts on the handle for alternately separating and bringing together the elongated jaws. In one configuration, the shape of each boot on its surface that faces the other jaw is convex. Preferably both boots have an outer surface shaped substantially as semicircles with the rounded portions facing one another.

In accordance with another aspect of the invention, a surgical apparatus for welding tissue includes first and second relatively movable elongated jaws having facing surfaces. The relatively movable jaws attach to a distal end of an elongated shaft, and at least one heating element is provided on the facing surface of one of the jaws. A control handle connects to the elongated shaft and a control actuator mounts on the handle for alternately separating and bringing together the facing surfaces of the elongated jaws. A fluid-mechanical driver connects between the control actuator and the jaws and translates movement of the control actuator into movement of the jaws.

A further aspect of the invention is a surgical apparatus for welding tissue comprising first and second relatively movable elongated jaws comprising inner jaw members surrounded by tissue-resistant boots. The relatively movable jaws attach to a distal end of an elongated shaft, and there is at least one heating element embedded in the boot of one of the first or second jaws. A control handle connects to the elongated shaft and a control actuator mounts on the handle for alternately separating and bringing together the elongated jaws.

Still further, another aspect of the invention comprises a surgical apparatus for severing tissue with first and second relatively movable elongated jaws having facing surfaces. The relatively movable jaws attach to a distal end of an elongated shaft, and at least one heating element is provided on the facing surface of one of the jaws. A control handle connects to the elongated shaft and a control actuator mounts on the handle for alternately separating and bringing together the facing surfaces of the elongated jaws. At least one flap projects from one of the jaws to overlap to the side of the opposite jaw when the jaws close and help push tissue from the jaws. Desirably, each jaw comprises an inner jaw member surrounded by a tissue-resistant boot, wherein each of the boots includes one of the flaps that projects to overlap to the side of the opposite jaw.

In accordance with still another aspect, a surgical apparatus for welding tissue is provided including first and second relatively movable elongated jaws having facing surfaces. The relatively movable jaws attach to a distal end of an elongated shaft, and at least one heating element is provided on the facing surface of one of the jaws. A control handle connects to the elongated shaft and a control actuator mounts on the handle for alternately separating and bringing together the facing surfaces of the elongated jaws. The control handle includes structure therewithin for temporarily locking motion of the control actuator at the extent of its movement when the jaws are closed. Preferably, the control actuator comprises a toggle adapted for pivoting movement within the control handle. The structure for temporarily locking motion of the toggle may comprise a pin on the toggle that rides in an L-shaped channel formed within the control handle, and a spring that biases the toggle into a short angled portion of the channel. Alternatively, the structure for temporarily locking motion of the toggle comprises a feature on the toggle that engages a pin fixed within the control handle.

Still further, the present invention provides a surgical apparatus for cutting tissue comprising first and second relatively movable elongated jaws having facing surfaces. The relatively movable jaws attach to a distal end of an elongated shaft, and at least one heating element is provided on the facing surface of one of the jaws for cutting through tissue when the jaws are open. A control handle connects to the elongated shaft and a control actuator mounts on the handle for alternately separating and bringing together the facing surfaces of the elongated jaws. A control rod extends from the control handle to the distal end of the elongated shaft and connects to translate movement of the control actuator into movement of the jaws. The control actuator includes a cam lobe that acts on the control rod and has a shape that, when displaced in one direction, opens the jaws to their maximum width and then slightly closes them to control the angle of the jaws relative to one another for improved cutting.

In a final aspect, the present invention provides a surgical apparatus for welding tissue comprising first and second relatively movable elongated jaws having facing surfaces. The relatively movable jaws attach to a distal end of an elongated shaft, and at least one heating element is provided on the facing surface of one of the jaws for cutting through tissue when the jaws are open. A control handle connects to the elongated shaft and a control actuator mounts on the handle for alternately separating and bringing together the facing surfaces of the elongated jaws. The apparatus further includes a circuit for energizing the heating element, the circuit having a safety interlock switch actuated on movement of the control actuator to fully close the jaws. Desirably, the safety interlock switch comprises at least one conductive pad mounted on the control actuator that contacts another conductive pad mounted within the control handle. Alternatively, the safety interlock switch comprises a switch, possibly a microswitch, mounted within the control handle in the path of movement of the control actuator.

BRIEF DESCRIPTION OF THE DRAWINGS

FIGS. 1A-1C are perspective views of a modular handle unit of a vessel harvesting system including a sled/adapter that permits a multipurpose handle base of the system to receive a tissue severing/welding device of the present invention;

FIGS. 2A-2B are perspective views of the distal end of an exemplary tissue severing/welding device of the present invention showing a pair of clamping jaws in their closed position;

FIGS. 3A-3B are perspective views of the distal end of the tissue severing/welding device of FIGS. 2A-2B showing the clamping jaws in their open position;

FIG. 4 is an exploded perspective view of the distal end of the tissue severing/welding device of FIGS. 2A-2B;

FIGS. 8A-8H are perspective, plan, and elevational views of an exemplary inner jaw forming a portion of the "hot" jaw of FIGS. 5A-5B;

FIGS. 9A-9E are perspective, plan, and elevational views of an exemplary heating element for welding tissue used in the "hot" jaw of FIGS. 5A-5B;

FIGS. 10A-10H are perspective, plan, and elevational views of an exemplary boot for covering the inner jaw of FIGS. 8A-8H;

FIG. 12 is a perspective exploded view of the proximal control handle of FIG. 11A;

FIGS. 15A and 15B schematically illustrate an exemplary force-limiting interface between an actuator of a control handle and a control rod that regulate the opening and closing of distal tissue welding jaws;

FIGS. 16A and 16B schematically illustrate another exemplary force-limiting interface in a toggle-like actuator of a control handle;

FIGS. 17A and 17B schematically illustrate another exemplary force-limiting interface in a toggle-like actuator of a control handle;

FIG. 18 schematically illustrates another exemplary force-limiting interface in a toggle-like actuator of a control handle;

FIG. 19 schematically illustrates another exemplary force-limiting interface between an actuator of a control handle and a control rod that forms a part of a toggle-like actuator and completely decouples movement of the control rod from further movement of the toggle beyond a predetermined reaction force;

FIG. 20 schematically illustrates another exemplary force-limiting interface between an actuator of a control handle and a control rod that also decouples movement of the control rod from further movement of the toggle beyond a predetermined reaction force;

FIG. 21 is a schematic view of a tubular control rod having a helical force-limiting spring cut therein;

FIGS. 22A and 22B schematically illustrate alternative exemplary force-limiting structures to control the opening and closing of distal tissue welding jaws located within an elongated shaft of the tissue welder;

FIG. 28 is a schematic depiction of a proximal end of tissue welding jaws having a spring between their respective pivot points for both limiting the force that can be applied thereby and helping to maintain parallelism of the jaws;

FIG. 29 is a schematic illustration of an actuator having a cam slot that acts on a control rod for displacing the control rod in a non-linear fashion;

DESCRIPTION OF THE PREFERRED EMBODIMENTS

Figure 5A:
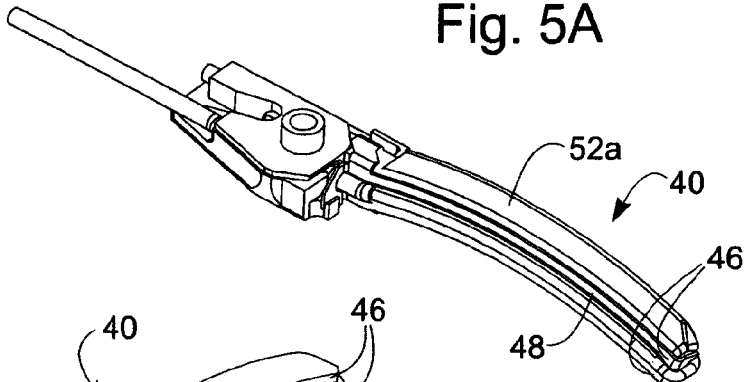
FIGS. 5A-5B are perspective views of a "hot" jaw used in the exemplary tissue severing/welding device of the present invention.

According to one aspect of the present invention devices and methods for sealing, or coagulating, and severing tissue during surgery are provided. The instruments incorporate means for controllably heating tissue while simultaneously applying a definite and controllable amount of pressure to the tissue being heated. Because of the combined application of heat and pressure, tissue proteins will become coagulated and blood vessels within the tissue will be sealed shut, achieving hemostasis. Optimal sealing or coagulating tissue means producing a strong and durable seal or coagulation or anastomosis with a minimal amount of collateral tissue damage.

One aspect of the present invention includes a method and system for the surgical treatment of biological tissue, wherein thermal energy and pressure are applied simultaneously, substantially simultaneously, consecutively, or alternatively, over a time such that tissue proteins are denatured and the tissue will adhere or join to itself or to other tissues, for the purpose of coagulating bleeding, sealing tissue, joining tissue and cutting tissue. The minimum amount of heat or thermal energy needed to accomplish these goals is expended, so as to minimize thermal damage to tissue adjacent to the treated site.

The devices of the invention may also incorporate means for cutting, or severing the tissue. "Severing" includes dissecting or tissue division, tissue disruption or separation, plane development, or definition, or mobilization of tissue structures in combination with a coagulation, or hemostasis or sealing of blood vessels or other tissue structures such as lymphatics, or tissue joining. Severing can be achieved by use of amounts of heat greater than the amount required to coagulate the tissues, yet a minimum amount of energy is used with the least amount of unwanted tissue necrosis. In conjunction with some aspect of the invention, severing can be achieved by other mechanical, ultrasonic, or electronic means, including, but not limited to, shearing action, laser energy, and RF, or a combination of two or more of the above. For example, a blade may be passed through the coagulated tissue while the tissue is being held in the jaws of the instrument.

The present invention desirably provides a tissue welder that can be incorporated as a component of an integrated vessel harvesting system, such as is disclosed in application Ser. No. 10/951,426, filed Sep. 28, 2004, which is expressly incorporated herein by reference. The vessel harvesting system is especially useful in minimally invasive endoscopic harvesting of blood vessels, including harvesting of internal thoracic artery, or vessels of the extremities along the radial artery in the arm for use in coronary artery bypass grafting, and the saphenous vein in the leg for use in both coronary artery bypass grafting and peripheral artery bypass. In this context, the tissue welder performs both a severing and securing/welding function in separating side branches from the target vessel that is being harvested. It should be understood, however, that various aspects of the tissue welder described herein may be utilized in conjunction with other surgical systems for coagulating and/or dissecting tissue.

The exemplary embodiment of the tissue welder of the present invention comprises a so-called "welding and severing device" that is used to close off and separate side branches from a primary vessel being harvested, and also possibly to sever the primary vessel. However, the device is disclosed herein are suitable for welding and severing tissue in general not just vessels. In its broadest sense, the term tissue welding and severing device refers to any and all devices that accomplish a single function or any combination of the functions of welding, ligating, cauterizing, coagulating and/or sealing, and severing or transecting target tissue. For example, electrocautery tools such as bipolar scissors (or other plural electrode-based devices), monopolar devices, tissue bisectors, or other such devices provide these functions alone or in conjunction with an integral blade or cutter. Other similar devices using various acceptable sources of energy for sealing the tissue (for example, RF, microwave, laser, ultrasound, direct thermal energy, etc.) are also within the scope of the present invention. Each device that acts on tissue to either weld or sever it will be termed an energy applicator. The welding and severing device could be a single tool or a combination of plurality of separate tools each having its own function useful in tissue severing, or more specifically in vessel harvesting.

Parenthetically, it is important to note that, while each of the various aspects of the present invention may be used to advantage in combination with the other aspects, each is believed to also be of patentable significance when used alone with otherwise conventional systems and techniques. Thus, the tissue welding devices and methods may be implemented using heating and control structures other than those disclosed herein, and in the context of systems other than those for vessel harvesting. Furthermore, various aspects of the tissue welder disclosed herein may be utilized with other welding and severing devices, such as bipolar scissors or tissue bisectors. Similarly, certain aspects of the coagulation function of the tissue welder may be combined with a mechanical cutter to provide the severing function.

Finally, it should be understood that the exemplary and/or alternative tissue welders and features described herein have numerous applications in addition to vessel harvesting. For example, a tissue welder may be utilized in gastric bypass surgery to resect and close a portion of the stomach. Similarly, volume reduction of the lungs in patients with emphysema can also be accomplished with the devices disclosed herein. Bowel resection is another potential application. Other surgical procedures include: femoral popliteal bypass; severing/ligating epigastric arteries for gastric reflux disease; fallopian tube ligation; vasectomies; severing/ligating arteries, veins, and bile ducts in gallbladder removal surgery; and nephrectomies where the ureters leading to the kidney are transected and ligated.

FIGS. 1A-1C illustrate a modular handle unit 20 of an exemplary vessel harvesting system comprising a mating handle base 22 and handle sled 24. The handle base 22 includes a distal flange 26 secured to an elongated cannula 28. The cannula 28 is sized to extend into a body cavity and provides a channel for various vessel harvesting tools. The handle sled 24 includes structure for mating with the handle base 22, as seen in FIG. 1A. Various modular handle units and vessel harvesting systems are illustrated and described in aforementioned application Ser. No. 10/951,426, filed Sep. 28, 2004.

In the particular embodiment of FIGS. 1A-1C, the handle sled 24 provides an adapter for multipurpose handle bases common to a number of vessel harvesting systems, such that a tissue welding and severing device 30 of the present invention may be used for vessel harvesting within the system. Specifically, the handle sled or adapter 24 provides a port 32 leading to an internal angled channel 34 through which the elongated shaft 36 of the welding and severing device 30 may extend. The handle base 22 and handle sled 24 couple such that the elongated shaft 36 is guided through the distal flange 26 and harvesting cannula 28. The final assembly as seen in FIG. 1C shows that some of the movement controls for the harvesting tools are located on the handle unit 20, while rotation of the welding and severing device 30 is accomplished by manipulating the entire handle 38 relative to the sled 24 with a second hand.

FIG. 1C also illustrates an enlarged distal end of the cannula 28 through which a distal end of the tissue severing/welding device 30 projects. The device 30 comprises a pair of relatively movable elongated jaws 40, 42 on its distal end, which are shown open. Preferably, a mechanism within the handle 38 includes an actuator 44 for opening and closing the jaws 40, 42. The jaws 40, 42 are elongated generally in a proximal-distal direction such that they are much longer in that direction than in either orthogonal or transverse axis.

It should be understood that the term "jaw" refers to a member that may be brought together with another similar member or other structure such that jaw-facing surfaces on both members are brought into contact or close proximity. A jaw may be provided on a clamp, tweezers, forceps, or similar grasping tools. The jaws 40, 42 are mounted such that their proximal ends are journalled about common or different but closely spaced pivots and their distal ends open and close. Of course, the jaws may be mounted for parallel movement instead of in a pivoting action. An exemplary embodiment of the present invention includes a "hot" jaw and a "cold" jaw, the difference being that only one jaw is actively heated. It should be emphasized, however, that certain aspects of the present invention are applicable to different jaw configurations, such as both being "hot" jaws, or both being "cold" jaws with a separate source of heat.

In a preferred embodiment, the first jaw 40 comprises a "hot" jaw, while the second jaw 42 is a "cold" jaw. The term "hot" refers to the presence of at least one active heating element thereon, while a "cold" jaw provides no active heating (but may become hot from indirect heating by the other jaw). In the illustrated embodiment, as seen in FIG. 1C, the first or "hot" jaw 40 includes a first heating element 46 for welding tissue and a second heating element 48 for severing tissue. The first heating element 46 is adapted to heat up to a first temperature upon application of current therethrough, while the second heating element 48 is adapted to heat up to a second temperature upon application of current therethrough which is greater than the first temperature. Conventional understanding is that when vascular tissue is heated in excess of 100° C., the tissue will be broken down and is thus, "cut". However, when vascular tissue is heated to temperatures between 50 to 90° C., the tissue will instead simply "seal" or "weld" to adjacent tissue.

Various means are described herein for ensuring that the first heating element 46 heats up to within a welding temperature zone but not to a cutting temperature threshold, while the second heating element 48 heats up past the welding temperature zone into the cutting temperature zone. For example, the relative electrical resistance values of the first and second heating elements 46, 48 may be such that they heat up to different temperatures. Alternatively, the materials used may be the same, but the first and second heating elements 46, 48 may be shaped in a manner that causes their differential heating. Still further, the current passed through the two heating elements may be unequal.

FIG. 1C also basically illustrates a preferred configuration of the jaws 40, 42 and a distal end of the shaft 36 extending through a distal end of the elongated cannula 28. In particular, the jaws 40, 42 are arranged to pivot apart about a common axis, represented by pivot pin 50. An exemplary mechanism for opening and closing the jaws 40, 42 will be described in detail below. Each of the jaws 40, 42 includes an inner jaw member of rigid material and a boot 52a, 52b (as seen in FIG. 3A) surrounding the inner jaw member that is made of the material that resists tissue adhesions during operation of the device. In one embodiment, the inner jaw members are made of stainless steel, but other materials that provide less of a heat sink may be used. Preferably, the boots 52a, 52b are made of a heat-resistant silicone rubber. The boots 52a, 52b also provide some thermal insulation around the inner jaw members to reduce heat losses thereto. The first and second heating elements 46, 48 are arranged external to the boot 52a on the first jaw 40, in particular on a surface of the jaw that faces the other jaw.

FIGS. 2-7 provide a number of assembled, exploded, and other partial views of the distal end of an exemplary tissue welding and severing device 30 of the present invention. In FIGS. 2A-2B, the jaws 40, 42 are shown closed at the distal end of the welding and severing device 30. The device 30 includes a generally tubular distal tip 54 that fits on the end of the device shaft 36 and houses a mechanism (described below) for opening and closing the jaws 40, 42. Both jaws 40, 42 exhibit a shallow curvature along their lengths such that their jaw-facing surfaces contact along a curved line. In a preferred embodiment, the entire distal assembly of the device 30 including the jaws 40, 42 is sized to fit through a 5 mm diameter port, thus enabling use in minimally invasive surgery.

The jaws 40, 42 preferably incorporate a multiple heater welding system on a "hot" jaw 40. At a minimum, at least two heating element are provided, with one heating element adapted to sever tissue and a second heating element adapted to weld or coagulate tissue. In an exemplary embodiment, the jaw 40 incorporates a "tri-heater" arrangement with one heating element for cutting and two heating elements for welding disposed on either side of the cutter. Desirably, the heating elements extend longitudinally from a proximal to a distal end of the jaw 40, with the cutter generally centrally located and the two welders symmetrically located on either side.

FIGS. 3A-3B illustrate the jaws 40, 42 in their open configuration. As can be seen in FIG. 3B, the first heating element 46 is preferably bifurcated into two welding members separated laterally, with a single second heating element 48 provided therebetween. The bifurcated welding members of the first heating element 46 each provide a weld region within the tissue, while the second heating element 48 cuts the tissue within the weld region. Technically, therefore, the hot jaw 40 includes three heating elements: a central cutting element and two adjacent welding elements. Although the exemplary embodiment combines the two adjacent welding elements in a single piece, they could easily be constructed separately. As mentioned above, one or both jaws 40, 42 include inner jaw members surrounded by a boot 52a, 52b. The boot 52b around the second jaw 42 is preferably provided with a series of lateral serrations 60 that facilitate gripping and prevent slipping of the tissue when clamped between the jaws. Because of the presence of the first and second heating elements 46, 48 on the exterior of the boot 52a on the first jaw 40, no serrations are necessary.

FIG. 4 shows the components of the distal end of the device 30 exploded, while FIGS. 5-7 best illustrate the specific shapes and subassembly of the first and second heating elements 46, 48, and how they mount on and cooperate with the first jaw 40. The inner jaw member 62 (seen isolated in FIGS. 8A-8H) of the first or "hot" jaw 40 comprises an elongated and curved distal portion 64 and a proximal pivot housing 66, including through holes for pivotal movement with respect to the other jaw. More specifically, the proximal pivot housing 66 of the inner jaw member 62 includes a large circular through hole 67 and an angled slot 68, both formed in an outer wall section 69. A pair of sidewalls 70 upstanding from the outer wall section 69 provide a space on the inner side of the pivot housing 66 within which electrical wires and a pivot mechanism are received, as explained below.

The first heating element 46 comprises a proximal crimp 72 and flange 73. Two elongated welding members 74 extend from the proximal crimp and flange in a distal direction and curl back upon themselves to terminate at a common barb 75 (see FIG. 7B). The elongated welding members 74 preferably comprise thin, rectangular strips each having a lateral width W that extend in parallel across a spaced distance S. Because the welding members 74 are connected at their proximal ends by the crimp 72 and flange 73 structure, and at their distal ends by the common barb 75, they define a bifurcated portion of the first heating element 46. In a preferred embodiment, the first heating element 46 comprises a single, homogeneous piece of metal (e.g., stainless steel) that has been formed into the illustrated shape by stamping, bending, machining, etc.

The second heating element 48 extends between and in parallel with the spaced welding members 74 and is separated therefrom by air gaps. The heating element 48 also extends in a distal direction the same length as the welding member 74 and curls back upon itself to terminate at a connection end 76 adjacent the barb 75 (see FIG. 7B). The connection end 76 and barb 75 are electrically connected using a resistance or spot weld, for example. In the context of the present application, the term "resistance weld" used to describe the joint between two mechanical parts encompasses all suitable varieties of such joints, including for example, spot welds, laser welds, soldered joints, brazed joints, etc.

As seen in the exploded view of FIG. 4, the heating element 48 may comprise an elongated wire or rod, and the connection end 76 may be formed by a separate U-shaped coupling 77 forming a series extension thereon. The second heating element 48 has a raised profile relative to the first heating element 46 in a direction toward the second jaw 42. This enhances the differential ability of the second heating element 48 to cut through tissue while the first heating element 46 welds. Furthermore, the strip-like welding members 74 of the first heating element 46 each have flat jaw-facing surfaces, while the second heating element 48 defines a cylindrical jaw-facing surface having a lateral width smaller than that of either welding member.

An exemplary first heating element 46 is seen isolated in FIGS. 9A-9E. These illustrations show a heating element 46 that is slightly different than the one shown in preceding figures, although either may be used with good results. The difference is in the distal end which exhibits a flange 78 that is bent, for example, at 90° instead of curling back into the barb 75 toward the proximal end. The flange 78 is forked to define a generally semi-circular opening 80 that receives the second heating element 48. Although not shown, in this version the second heating element 48 curls 180° into the opening 80 and is secured in electrical contact therewith using a resistance weld, for example.

Figure 5B:
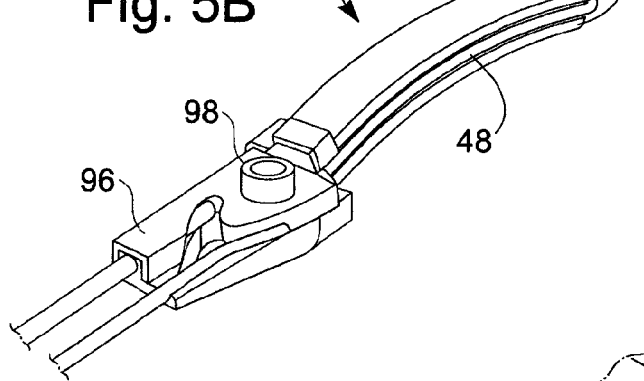
Figure 6A:
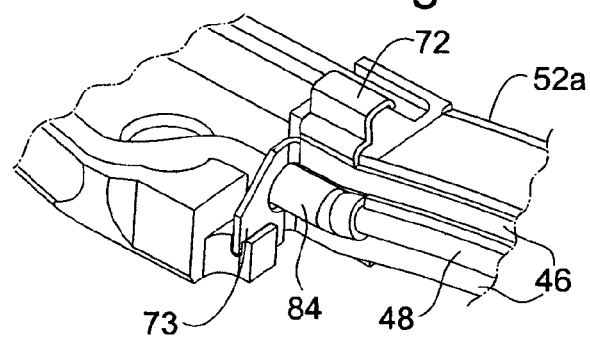
FIGS. 6A-6B are enlarged perspective views of a proximal subassembly of the "hot" jaw of FIGS. 5A-5B.
Figure 6B:
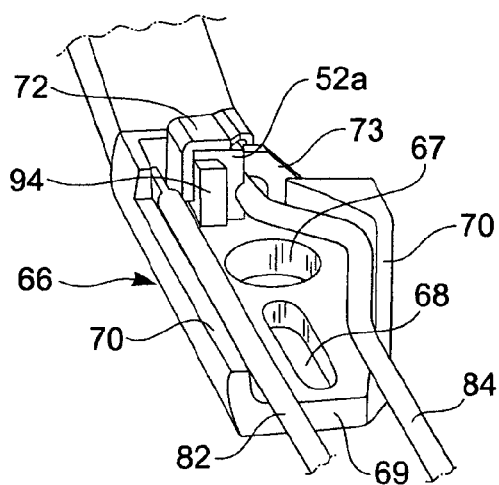
Figure 7A:
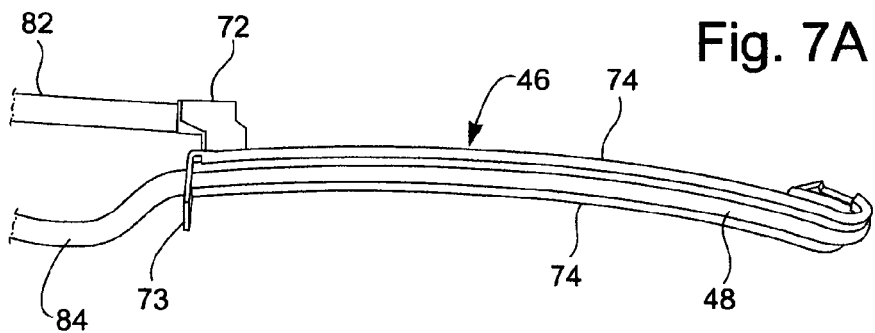
FIGS. 7A-7C are perspective views of an exemplary heating element subassembly of the "hot" jaw of FIGS. 5A-5B.
Figure 7B:
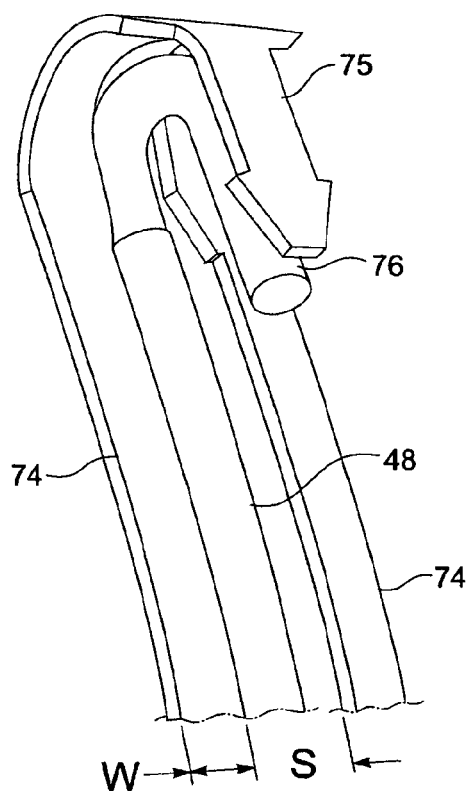
Figure 7C:
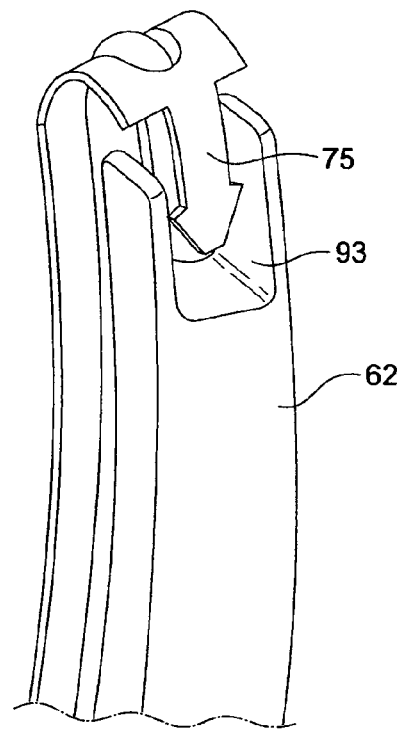

Now with specific reference to FIGS. 5-7, the heating elements 46, 48 are shown having conductor wires attached thereto to form a series circuit. As seen in FIGS. 6B and 7A, a pair of insulated conductor wires 82, 84 form part of a circuit path through the heating elements 46, 48. The first conductor wire 82 is in electrical communication with the first heating element 46 by virtue of a resistance weld at the proximal crimp 72, while the second conductor wire 84 is in electrical communication with the second heating element 48. An insulated sleeve around the second conductor wire 84 extends through an aperture formed in the flange 73 of the first heating element 46. The barb 75 and connection end 76 are electrically connected such that the first and second heating element 46, 48 define a current loop all along the length of the jaw 40.

Current through the conductors 82, 84 therefore passes in series through the first and second heating elements 46, 48. Current through the two heating elements 46, 48 remains separated to the common distal end thereof, and in particular to the resistance weld between the barb 75 and connection end 76. Because of the bifurcation of the first heating element 46 into the separate welding members 74, each of the welding members 74 conducts in parallel approximately half of the current that passes through the second heating element 48. It should be understood, therefore, that if the heating elements are identical in shape and material, each welding member 74 would heat up to a temperature less than that which the second heating element 48 attains because of the split current. This differential helps ensure that the first heating element 46 reaches the welding zone temperatures, while the second heating element 48 reaches temperatures within the cutting zone. In the illustrated embodiment, the separate welding members 74 each have a wider profile (i.e., larger surface area) facing the tissue in a plane transverse to the direction of elongation of the jaw 40 than does the second heating element 48. This structural difference in conjunction with the lower current and thus lower temperature helps facilitate a welding action on the tissue as opposed to a cutting action, in contrast to the central heating element 48 which is both narrower and hotter (and raised up higher).

Advantageously, however, the second heating element 48 is constructed so as to have a higher electrical resistance than either of the welding members 74, and therefore even more of the already larger current dissipates as heat. This combined phenomena of higher current and higher resistance causes the second heating element 48 to heat up to a cutting temperature zone, while the first heating of the 46 only reaches temperatures in the tissue welding zone. In a preferred embodiment, the first heating element 46 is made of a suitable conductive metal such as 301 stainless steel, while the second heating element 48 comprises a tube of rigid material with filler having a higher magnitude of electrical resistance than the tube, the combination having an electrical resistance greater than stainless steel. In one specific embodiment, the tube is made of a nickel-chromium alloy such as INCONEL 625 and is filled with an electrically insulating but thermally conductive ceramic such as magnesium oxide (MgO) powder. Consequently, a greater current density passes through the hollow tube than if it were solid, and therefore the material reaches a higher temperature at any given current. Additionally, the inner thermally conductive ceramic does not unduly restrict conductive heat flow through the element 48. Preferably, the second heating element 48 has a relatively high resistance of about 0.2 Ohms, and the entire system of the first and second heating elements has an average resistance of about 0.72 Ohms, and preferably less than 0.8 Ohms.

It is important to understand that the present invention contemplates at least one cutting element and at least one welding element, electrically connected in series or not. For example, the illustrated embodiment may be modified by utilizing two current paths, one for the first (welding) heating element 46 and one for the second (cutting) heating element 48. Alternatively, one cutting element and a single (i.e., not bifurcated) welding element may be provided on the hot jaw, both forming a part of a common current path. Finally, the same arrangement can be utilized with separate current paths. Moreover, as mentioned above, the cutting element may be provided on one jaw while the welding element is provided on the opposite jaw. In each of these alternative configurations, the common denominator is that upon application of a common or separate currents, the cutting element reaches a higher temperature than the welding element.

FIGS. 10A-10H show a number of views of an exemplary boot 52a used on the "hot" jaw 40. As mentioned above, the boot 52a is made of material such as silicone rubber that resists tissue adhesions, and thus facilitates multiple tissue severing/welding operations prior to a reduction in the effectiveness of the jaws because of such tissue adhesions. The boot 52a provides electrical insulation between the heating elements 46, 48, and also provides thermal insulation, thus helping to retain heat to the space between the jaws as opposed to being lost to the often metallic inner jaws 62. The boot 52a generally comprises a hollow sleeve having an open proximal end 86 and a partially closed distal end 88. An upper surface 90 that faces the cold jaw 40 when the boot 52a is mounted on the hot jaw 40 includes a pair of longitudinally-oriented rails 92. As seen in FIGS. 10D and 10G, the rails 92 are generally evenly spaced apart and provide guide channels for the bifurcated first heating element 46 and the central second heating element 48. The distal end 88 of the boot 52a has an opening into which extend the joined and curled or bent distal ends of the two heating elements 46, 48. This holds the distal ends of the two electrodes on the hot jaw 40. It should be noted that the distal end of the inner jaw member 62 has a forked depression as seen at 93 in FIG. 7C. The insulating boot 52a is molded so that it has an inside shape which conforms within this depression 93, and also provides an outwardly opening cavity to receive the joined barb 75 and connection end 76. The arrowhead shape of the barb 75 helps secure the heating elements in place with respect to the soft insulating boot 52a, which, again, is preferably silicone rubber.

FIGS. 5-6 illustrate the integration of the combined heating elements 46, 48 and conductor wires 82, 84 into the inner jaw member 62. As seen best in FIG. 6B, the proximal crimp 72 secures the first heating element 46 and an extension of the silicone boot 52a to an upstanding flange 94 of the pivot housing 66. The conductor wires 82, 84 are routed through the space in the pivot housing 66 formed by the pair of sidewalls 70. The first conductor wire 82 extends straight along one side wall 70 and is resistance welded or otherwise secured to the proximal crimp 72 of the first heating element 46. The second conductor wire 84 follows a bent path along the other side wall 70 and passes through the aforementioned aperture formed in the proximal flange 73 of the first heating element 46, as seen in FIG. 6A. FIG. 5B shows a bushing 96 having an upstanding shaft stub 98 assembled over the pivot housing 66. The bushing 96 forms a part of a mechanism for opening and closing the jaws 40, 42, and will be more clearly described below.

One aspect of the present invention that facilitates assembly and thus reduces fabrication cost, is the integrated nature of the heating element subsystem. The subsystem is seen in FIGS. 6B and 7A, and consists of five parts: the first heating element 46, the second heating element 48, the pivot housing 66 (typically fabricated integral with the first inner jaw 62), and the two wires 82 and 84 that provide current through the series heating elements. These five parts are held together with several crimps, or desirably resistance welds, or both, and may be easily assembled prior to integration with the rest of the hot jaw 40.

As mentioned above, either or both of the jaws 40, 42 includes an inner jaw member covered with a boot. The exploded view of FIG. 4 shows both the inner jaw member 62 of the hot jaw 40, and an inner jaw member 102 of the second or "cold" jaw 42, along with the associated boots 52a, 52b. Both boots 52a, 52b fit over and surround the curved distal portions of the inner jaw members 62, 102, respectively.

In prior tissue welders, stainless steel inner jaw members were conveniently used as the return conduction path for the current passing through one or more electrodes. This had a distinct disadvantage in that some of the current was dissipated as resistance heat generated within the inner jaw member. This also had a disadvantage of heat conduction from heating element into jaw that resulted in less efficient energy delivery to tissue and potential inadvertent thermal injury. In one aspect the present invention not only physically decouples the heating elements 46, 48 from the first inner jaw member 62, in that a layer of the insulating boot 52a is interposed therebetween, but no current runs through the inner jaw member. The series connection between the distal barb 75 and connection end 76 means that the entire electrical conduction path along the hot jaw runs only through the heating elements 46, 48. In this way, the efficiency of conversion of electrical energy into desirable resistance heat is maximized, and the footprint of the device on tissue other than that directly in contact with the heating elements is minimized.

In addition to being able to weld and sever tissue, and in particular blood vessels, the jaws 40, 42 may also be capable of performing fasciotomy, or an incision through fascia (e.g., bands or fillets of fibrous tissue that separate different layers of tissue). As seen best in FIG. 3B, where the jaws 40, 42 are shown open, the second heating element 48, the "cutter wire," extends the full-length of the jaw along its midplane. In addition, it is positioned so as to be raised upward from the surrounding weld members of the first heating element 46 and thus presents the first surface of the hot jaw 40 to contact tissue received within the jaws. Fasciotomy can be performed by merely pushing the open jaws through a band of tissue with the second heating element 48 energized such that it cuts the tissue by heating it above the cutting temperature. Of course, in the exemplary embodiment the first heating element 46 also heats up, although this will have negligible impact on the fasciotomy procedure.

FIG. 4 also illustrates a tapered tip 103 on the distal end of the inner jaw member 102 of the second or "cold" jaw 42. This tip 103 helps facilitate blunt dissection of tissue when the device is used as such. The surrounding boot 52*b* will have a similar taper. In a preferred embodiment, the inner jaw member 102 has a generally rectangular cross-section, and the tip 103 has two tapers provided on the opposite straight sides. Of course, other arrangements such as a more rounded cross-section and a conically-tapered tip 103 may be substituted. Moreover, the inner jaw member 102 of the cold jaw 42 is slightly longer than the more blunt inner jaw member 62 of the first jaw 40 to further ease dissection of tissue.

Attachment of the jaws 40, 42 to the distal end of the tissue welder shaft 36, and an exemplary mechanism for opening and closing the jaws will now be described. With reference to the exploded view of FIG. 4, and also to FIGS. 3 and 5, the pivot housing 66 of the first inner jaw member 62 comes together with a proximal pivot housing 104 of the second inner jaw member 102, capturing the bushing 96 therebetween. The bushing 96 includes oppositely directed shaft stubs 98 that fit within the aligned apertures formed in the pivot housings 66, 104, such as the aperture 67 seen in FIG. 6B. The bushing 96 includes features on one side that mate with the particular shape of the pivot housing 66 and conductor wires 82, 84 arranged therein. In this regard, the bushing 96 is fixed with respect to the pivot housing 66 of the first inner jaw member 62. The pivot housing 104 of the second inner jaw member 102, on the other hand, includes a flat lower surface that slides across a flat upper surface of the bushing 96 when the housing pivots about the shaft stub 98. Consequently, the first inner jaw member 62 and second inner jaw member 102 are permitted to pivot with respect one another about the shaft stubs of the bushing 96.

The exploded view of FIG. 4 also shows the distal end of the flexible shaft 36 which includes a stepped-down portion 110. The flexible shaft 36 is hollow and receives a control rod 112 therethrough. A generally Y-shaped yolk 114 attaches to the distal end of control rod 112 through a resistance weld or similar expedient (not shown). Linear movement of the control rod 112 therefore also moves the yolk 114. The generally tubular shaft tip 54 fits over the stepped-down portion 110 and is secured thereto with a rivet 118.

With reference primarily to FIG. 4, but also FIGS. 2 and 3, the tubular shaft tip 54 includes a bifurcated distal end having a pair of arms 120 defining side openings 122 therebetween. As will be explained, the pivot housings 66, 104 of the jaws extend between the arms 120 and the side openings 122 permit pivotal movement thereof. The assembly of the two pivot housings 66, 104 with the bushing 96 therebetween is sandwiched between a pair of small spacers 124 that have flat inner surfaces and partial cylindrical outer surfaces. The spacers 124 include through bores that align with the apertures 67 in the pivot housings and with the inserted shaft stubs 98. The jaw assembly including spacers 124 then fits between the bifurcated arms 120 and is secured therein with a rivet 126 that passes through a pair of apertures 128 in the fingers, and through the aforementioned apertures. The jaws 40, 42 therefore pivot about the shaft stubs 98.

Both of the pivot housings 66, 104 include the angled slots 68 that are generally aligned with elongated slots 130 formed in both of the arms 120 of the shaft tip 54. As seen in the exploded view of FIG. 4, the angled slots 68 are oppositely oriented with respect to one another. The combined thickness of the assembled pivot housings 66, 104 fits between the bifurcated fingers of the yolk 114 and a rivet 132 passes through apertures in the distal ends of the yolk fingers and through the angled slots 68. In this way, linear movement of the yolk 114 translates into linear movement of the rivet 132, which in turn opens and closes the jaws 40, 42 through a camming action in the angled slots 68. The elongated slots 130 provide clearance for the rivet heads, ensure planar alignment of the rivets, and also facilitate assembly thereof. With the angled slots 68 oriented as shown, the jaws will be open when the control rod 112 is displaced distally, while proximal movement of the control rod closes the jaws.

Electricity can be delivered to the jaws 40, 42 through the conductor wires 82 and 84, best shown in FIG. 6B, or directly through the pivoting mechanism just described. For example, the control rod 112 may be electrically conductive and provide current to the inner jaw members and 62, 102 via the connecting the yolk, pins, and angled slots. The return current path might be provided by a single conductive wire. The illustrated embodiment utilizing conductor wires 82, 84 is preferred because it eliminates moving parts from the electrical conduction path.

Within the constraints of the small diameter design (less than 5 mm), the jaw movement mechanism should be relatively robust to be capable of applying a closing force of around 1-3 lb, preferably about 1 lb, and an opening force of around 1-3 lb. Further, the jaw opening distance at the distal tips thereof is desirably about 8 mm. In addition to welding and cutting tissue, the jaws can also be used for blunt dissection because of the tapered and rounded outer shape of the jaws. This blunt dissection can also be enhanced by the relatively robust opening force provided by the jaws.

As will be apparent, the jaw opening and closing function can be achieved in many different ways. The present invention, in its broad interpretation, is not particularly limited to any one type of mechanism. For example, instead of both jaws pivoting about a common axis, a series of linkage members may be utilized with the jaws pivoting about spaced axes. The form of jaw opening apparatus is preferably chosen to minimize cost and optimize transfer of linear force to pivoting movement of the jaws. Optionally, the pivoting mechanism is configured such that the jaw-facing surfaces of the jaws remain parallel.

An exemplary control handle 38 seen in FIGS. 11A-11C and 12 contains a mechanism for actuating the control rod 112 and opening and closing the jaws, in addition to several other desirable features. The control handle 38 is seen in elevation and two opposite partial sectional views in FIGS. 11A-11C. The control handle 38 includes an outer housing 140 formed by the juxtaposition of two molded housing halves 140*a*, 140*b*. The outer housing 140 includes a plurality of walls and/or bulkheads 141 that defined therebetween a series of internal housing cavities. A distal through bore formed in the outer housing receives the flexible shaft 36 leading to the distal jaws 40, 42. The aforementioned actuator 44, in the illustrated example, is journalled to pivot about a pin 142 fixed with respect to the housing, and includes a thumb pad 144 opposite the pin 142. A narrow section of the actuator 44 travels within a proximal-distal slot 146 in the housing 140 such that the thumb pad 144 provides a slider for the user. The actuator 44 is therefore constrained to pivot in a hollow space between the two housing halves 140*a*, 140*b* and the thumb pad 144 travels between opposite ends of the slot 146. Movement of the slider 144 in a distal direction (to the left in FIG. 11A) closes the jaws, while movement of the slider in the proximal direction (to the right in FIG. 11A) opens the jaws.

The exemplary control handle 38 includes circuitry for energizing the aforementioned heating elements at the distal end of the tool in addition to the mechanism for opening and closing the jaws. Although the invention is not limited to one particular switching arrangement, the exemplary embodiment includes a weld/cut switch that actuates both the welding heating element and the cutting heating element simultaneously, and coincident with the jaw closed position. Moreover, the control handle 38 includes a governor for limiting the force that can be applied by the jaws on tissue held therebetween.

Figure 11A:
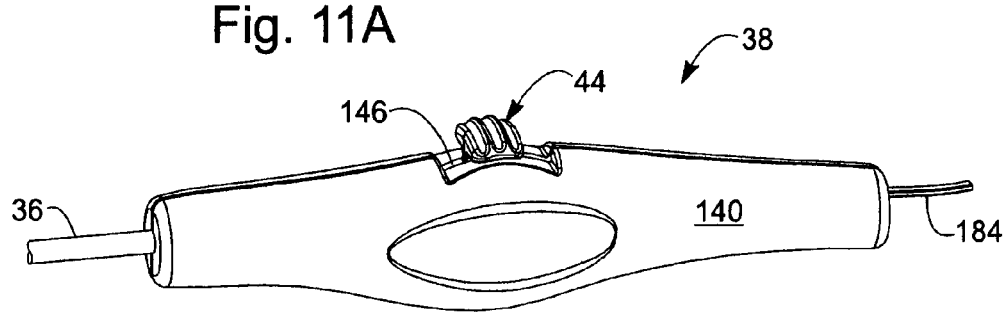
FIG. 11A is a perspective view of a proximal control handle of an exemplary tissue severing/welding device of the present invention.
Figure 11B:
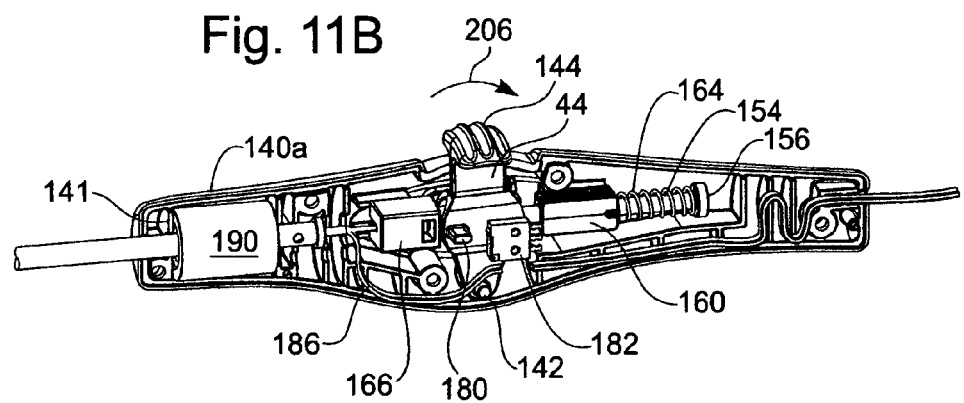
FIGS. 11B-11C are opposite longitudinal sectional views of the control handle of FIG. 11A including a passive smoke filter therein.
Figure 11C:
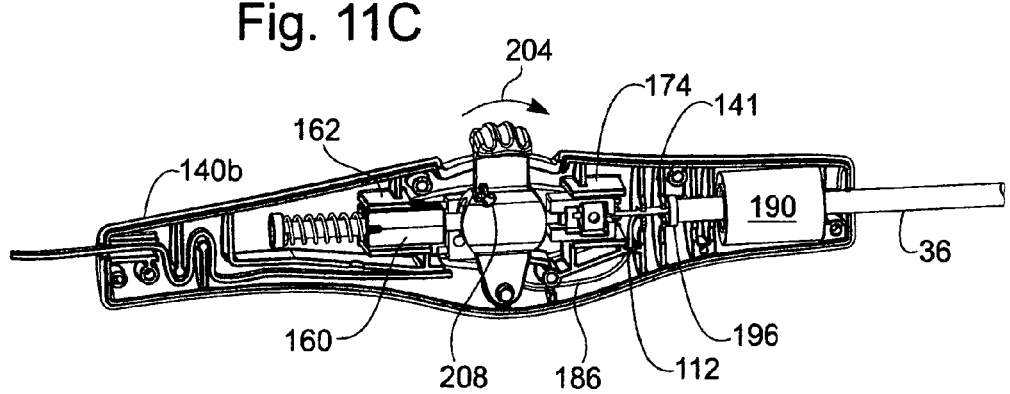

With reference still to FIGS. 11A-11C, and in particular the exploded view of FIG. 12, the actuator 44 possesses an enlarged mid-section 150 having a vertically elongated proximal-distal through bore 152 defined therewithin. The through bore 152 receives therein a rod 154 having a proximal head 156 and a distal head 158. The proximal end of the rod 154 extends through a force transfer block 160 and into a cavity to the proximal side of the actuator 44. The force transfer block 160 translates in a proximal-distal direction between a pair of guide walls 162 formed in the housing and includes a bore that slides over the rod 154. A force-limiting spring 164 closely surrounds the rod and is constrained between the proximal head 156 and the force transfer block 160. The distal end of the rod 154 extends to the distal side of the actuator 44 such that the distal head 158 is captured within a force coupler 166. FIG. 12 illustrates best the internal contours of the generally box-shaped force coupler 166 which includes a large cavity, a smaller cavity in which the distal head 158 is received, and a pair of slots on opposite ends thereof (elements not numbered for clarity). One side of the force coupler 166 is removed to facilitate assembly of the cooperating parts, as seen in FIG. 11C. Like the force transfer block 160, the force coupler 166 translates in a proximal-distal direction between a pair of guide walls 174 formed in the housing.

With specific reference to FIG. 11B, a small tang 180 projects laterally from the enlarged mid-section 150 of the actuator 44. The tang 180 is positioned to engage and trip a weld/cut switch 182 mounted within the housing 140. That is, the switch 182 is fixed with the respect to the housing 140, while the tang 180 pivots with the actuator 44. When the thumb pad 144 translates in a proximal direction within the slot 146, the actuator 44 pivots in a clockwise direction until the tang 180 actuates the lever of the weld/cut switch 182. An electrical wire 184 extends into the proximal end of the handle 38 and provides power to the switch 182. From there, an electrical lead 186 continues in the distal direction and passes through the flexible shaft 36 to the heating elements on the jaws at the distal end of the tool.

FIGS. 11B and 11C illustrate a cylindrical filter 190 captured between bulkheads 141 at the distal end of the housing 140. The generally tubular filter 190 is seen exploded in FIG. 12, and includes a stepped through bore 192 that receives, on either end, a pair of O-rings 194. The O-rings 194 each have an inner diameter that closely fits and seals around the flexible shaft 36. The shaft 36 extends into the distal end of the housing 140, through the filter 190, and terminates at a seal 196 adjacent one of the bulkheads 141 of the housing. As shown in FIG. 11C, the control rod 112 continues through the seal 196 and into the force coupler 166. A collar 200 received in the large cavity of the force coupler 166 fastens to the proximal end of the control rod 112 with a set screw 202. In this manner, the proximal end of the control rod 112 is constrained by the collar 200 within the force coupler 166.

In use, the operator slides the thumb pad 144 in a distal direction along the slot 146 as seen by arrow 204 in FIG. 11C to pivot the actuator 44 and open the jaws of the tool. As the actuator 44 pivots, its angular movement is accommodated by the elongated through bore 152 over the rod 154. A curved distal face of the enlarged mid-section 150 eventually contacts the proximal end of the force coupler 166 and acts as a cam to urge it in a distal direction. Because the collar 200 is constrained within the larger cavity of the force coupler 166, it also translates in a distal direction which, in turn, pushes the control rod 112 distally. In this embodiment, there is no clutch or force-limiter interposed between the actuator 44 and distal movement of the control rod 112 to open the jaws. Therefore, the extent that the jaws open is limited by the extent of travel of the thumb pad 144, or by the hinge mechanism of the jaws themselves.

Conversely, the operator slides the thumb pad 144 in a proximal direction along the slot 146 as seen by arrow 206 in FIG. 11B to pivot the actuator 44 and close the jaws of the tool. A curved proximal face of the enlarged mid-section 150 eventually contacts the distal end of the force transfer block 160 and acts as a cam to urge it in a proximal direction. Because the force transfer block 160 is free to slide over the rod 154, it moves in a proximal direction toward and compresses the spring 164. Compression of the force-limiting spring 164 applies a proximally-directed force to the proximal head 156 of the rod 154. Because the distal head 158 is constrained within the stepped cavity of the force coupler 166, which in turn is connected to the control rod 112, the resistance to proximal displacement of the rod 154 is provided by any force resisting closure of the jaws (assuming minimal frictional forces acting on the control rod 112). Prior to the jaws clamping any tissue, this resistance to proximal displacement of the rod 154 is minimal and proximal displacement of the force transfer block 160 translates into equivalent displacement of the control rod 112. However, when the jaws finally close on tissue, the maximum closing force of the jaws is limited by the stiffness of the spring 164. Specifically, after the jaws close a constant force is applied to the tissue therebetween because of the spring 164.

Through careful calibration of the force-limiting spring 164 in conjunction with the particular jaws on the tool, this closing force can be limited to less than that which would unduly crush or otherwise cause trauma to the tissue within the jaws. Those of skill in the art will understand that it is the pressure applied to the tissue that must be limited, and that the pressure partly depends on the shape and size of the jaws, as well as the elastic constant of the spring 164. Desirably, the force imparted on tissue by the jaws is between about 1-3 lbs (0.45-1.36 kg), and preferably about 1 lb, as regulated by the spring 164. This preferred range of force ensures the heating elements effectively weld and sever tissue held within the facing surfaces of the jaws in a reasonably short amount time, preferably within 5 seconds or less. That is, applying a force of less than 1 lb to tissue tends to delay the cutting function, while application of a force greater than 3 lbs tends to sever the tissue before an effective weld is formed. Again, this preferred force range and operation time to depend upon the size and shape of the jaws. However, given the constraints of endoscopic tissue welding, in particular during vessel harvesting procedures, these parameters are believed to encompass a wide range of suitable jaw types.

To better explained the desirable weld parameters of the tissue welder, the reader is directed back to FIGS. 8A-8H showing the inner jaw member 62 of the hot jaw, and FIGS. 10A-10H showing the boot 52a that covers the inner jaw member 62. The inner jaw member 62 has the curved distal portion 64 extending from the proximal pivot housing 66, and a length from the circular pivot hole 67 to its distal tip of approximately 0.740 inches (18.80 mm). As mentioned above, the inner jaw member 102 of the cold jaw 42 is slightly longer than the more blunt inner jaw member 62 of the first jaw 40 to ease dissection of tissue, and preferably has a length of approximately 0.765 inches (19.43 mm). Desirably, the jaw member 62 is made of stainless steel, although other materials, thermally conductive or otherwise, may be utilized. The transverse cross-sectional shape of the distal portion 64 is approximately square adjacent the pivot housing 66, having a dimension on each side of approximately 0.060 inches (1.52 mm).

The dimension of the tissue-facing side of the distal portion 64, seen in FIG. 8E, remains constant along the length of the jaw member 62, while the perpendicular dimension seen in FIGS. 8D and 8F gradually tapers smaller toward the distal tip to a final dimension of about 0.031 inches (0.79 mm). The boot 52a seen in FIGS. 10A-10H has an overall length sufficient to cover the curved distal portion 64, and a transverse tissue-facing width of approximately 0.082 inches (2.083 mm). The dimensional parameters of the boot 52b of the cold jaw are equivalent, although the two boots perform different functions and are thus configured differently.

The previously mentioned desirable clamping force of the jaws of between 1-3 pounds can also be characterized in terms of pressure on the tissue to produce the most effective balance between severing and welding. Using the approximate dimensional values given above, the jaws desirably exert a pressure on the tissue of between about 25-75 psi, averaged transversely across the tissue-facing surfaces of the boots 52a, 52b. It should be understood that this range is an estimate based on the non-uniform contours of the tissue-facing surfaces of the boots 52a, 52b, and those of skill in the art will understand that structural modifications to the jaws may affect the preferred force and/or pressure range. Moreover, the temperature to which the heating elements on the jaws rise also affects the preferred force applied, as well as the duration of the weld. Once again, a commonly accepted range of temperatures at which human tissue may be welded is 50 to 90° C., while severing occurs at temperatures of 100° C. and above. Using these guidelines, if the exemplary jaws apply a clamping force of between 1-3 pounds on tissue and the welding and severing heating elements are energized to these temperatures, a preferred duration of weld is between 1-5 seconds. If the clamp duration is too short, the weld may not be effective and the tissue is less likely to completely sever, while an excessive duration above 5 seconds may tend to char tissue.

Still with reference to FIG. 11B, movement of the actuator 44 in the direction of arrow 206 also displaces the tang 180 into engagement with the weld/cut switch 182. Even if the intervening force-limiting spring 164 limits further closure of the jaws, the actuator 44 can continue movement until the switch 182 is tripped. The control handle 38 of the present invention further includes feedback to indicate to the user aurally and via tactile sensation through the thumb pad 144 when the switch 182 has been tripped, both on and off. More particularly, FIGS. 11C and 12 illustrate a small protrusion 208 projecting laterally from the actuator 44. This protrusion pivots along with the actuator and engages a small tooth 210 provided on a pivoting detent lever 212 (see FIG. 12). Although not shown in FIG. 11C, the detent 212 pivots about a point fixed within the housing 140 and the tooth 210 is biased upward by a detent spring 214. The protrusion 208 cams past the tooth 210 which displaces and provides both an audible and tactile click to the user at the point that the switch 182 is tripped ON. Movement of the actuator 44 in the opposite direction also causes the protrusion 208 to cam past the tooth 210, thus indicating when the switch 182 is turned OFF. In an exemplary procedure, the weld time is typically less than 5 seconds.

The exemplary control handle 38 illustrated in FIGS. 11A-11C and FIG. 12 further includes a system for capturing smoke or particulate matter that is generated by the distal jaws at the operating site within the tissue cavity. As mentioned above, various end effectors may be utilized with certain aspects of the present invention, with resistance heating elements being featured as the exemplary embodiment. Most of these end effectors, including resistance heating elements, often cause a substantial amount of smoke to be generated from the heated tissue. Furthermore, the operation is typically performed using $CO_2$ insufflation which creates a pressure gradient forcing gas in a proximal direction through the flexible shaft 36.

To control egress of this smoke through the flexible shaft 36, the control handle 38 provides the aforementioned passive filter 190. The flexible shaft 36 includes at least one gas escape port 220 at its proximal end. This port 220 is positioned between the O-rings 194 and within the hollow interior of the filter 190. The hollow cavity within the filter 190 provides a venting chamber or space to receive the gasses from the port 220. In addition, the proximal end of the flexible shaft 36 is capped by the seal 196 which conforms closely around the control rod 112 and electrical lead 186. All of these seals force any gas (and smoke or particulate matter) traveling proximally through the flexible shaft 36 to exit through the gas escape port 220. Consequently, the gas is forced through the gas permeable material of the filter 190 which traps any smoke or particulate matter before it reaches the interior of the housing 140. From there, the now filtered gas, predominantly $CO_2$, passes through the various cavities within the housing 140 and exits through random fissures and openings therein.

Figure 11D:
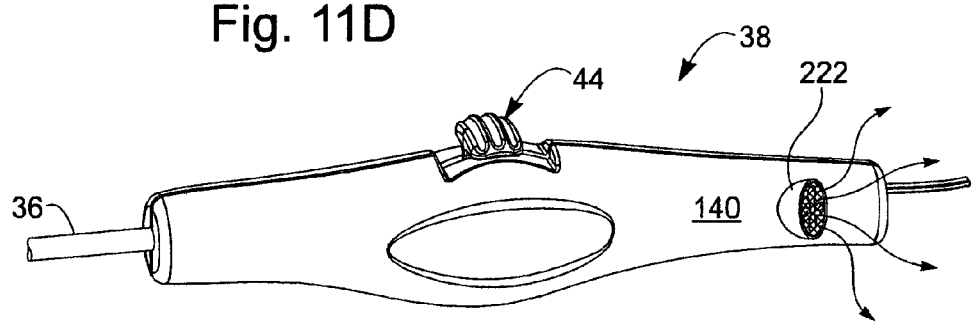
FIGS. 11D-11F illustrate control handles having alternative smoke filter configurations.
Figure 11E:
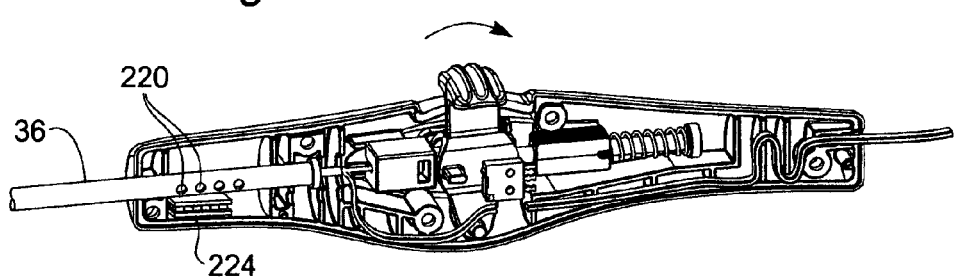
Figure 11F:
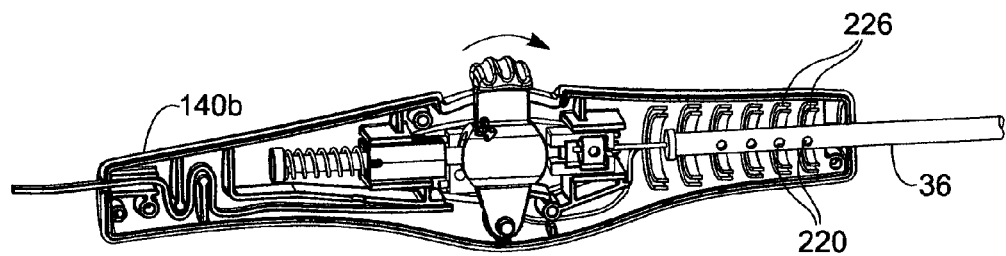

Several alternative configurations for filtering smoke generated by the tissue welding procedure are seen in FIGS. 11D-11F. First of all, FIG. 11D illustrates the exemplary control handle 38 having a small exhaust fan 222 mounted near its proximal end. The exhaust fan 222 helps pull gas passing through the elongated shaft 36 through the aforementioned passive filter 190. In many instances means for gas insufflation is provided in the overall system within which the tissue welders is used, which provides a positive pressure within the body cavity and forces gas proximally through the elongated shaft 36. However, in some procedures either no insufflation is used or it does not generate sufficient pressure, in which case the auxiliary fan 222 helps pull the gas through the filter 190.

FIG. 11E illustrates the interior of an alternative control handle in which a cooling apparatus 224, such as a Peltier cooler, is mounted adjacent the gas escape ports 220 in the elongated shaft 36. The smoke emitted from the port 220 connect is on the cooling apparatus 224, which effectively passively filters the gas which is then permitted to exit from various openings in the handle.

Alternatively, FIG. 11F illustrates a further alternative control handle in which a plurality of louvers or fins 226 are arranged adjacent the gas escape ports 220. The fins 226 diffuse and condense the smoke traveling proximally through the elongated shaft 36, and thus act as a passive filter. The gas is then permitted to exit from various openings in the handle. Because the surface area through which the smoke exhausts is expanded, the density of that smoke is decreased making it less noticeable as it exits the handle. In the illustrated embodiment, the fins 226 are configured as a series of concentric annular elements, but other arrangements are possible.

Figure 13A:
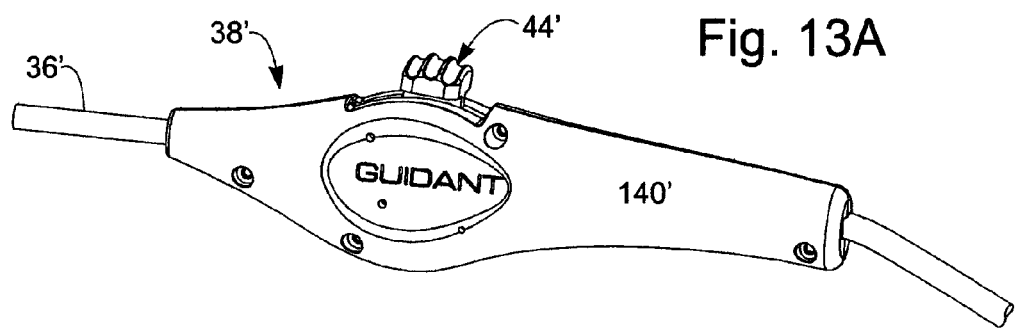
FIG. 13A is a perspective view of an alternative control handle of the present invention.
Figure 13B:
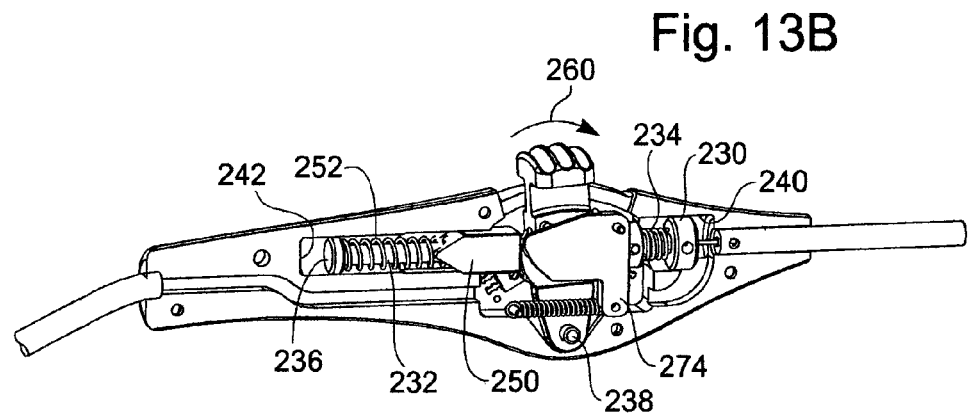
FIGS. 13B-13C are opposite longitudinal sectional views of the control handle of FIG. 13A.
Figure 13C:
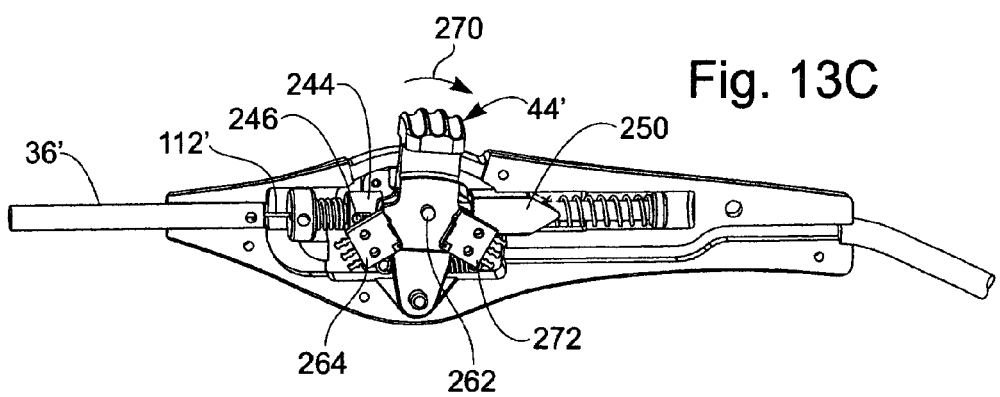

FIGS. 13A-13C illustrate an alternative control handle 38' similar to that described above but including a separate electrical circuit for a fasciotomy cutter provided on a distal tool. As mentioned above, fasciotomy comprises an incision through fascia (e.g., bands or fillets of fibrous tissue that separate different layers of tissue). The tissue welding/cutting jaws may also be adapted to include such a fasciotomy cutter which enables the tool to be moved linearly through to cut tissue without opening and closing the jaws. The fasciotomy cutter may be a separate heating element provided on the forward end of one of the jaws, or within the jaws. Some of the elements illustrated for the alternative control handle 38' are common to the control handle 30 described above with respect to FIGS. 11-12, and therefore will be given the same element number with a prime "'" designation.

As seen in FIGS. 13B-13C, the flexible shaft 36' from the distal tool enters the molded housing 140', and a control rod 112' projects therefrom into a cavity formed within the housing and is fixed to an enlarged collar 230. Although not shown, a shaft member 232 fastened to the collar 230 extends in a proximal direction through a fasciotomy spring 234, and through an actuator 44' to terminate at a proximal head 236. The actuator 44' is much like the actuator 44 described above, with a body that pivots about a pin 238 and has an elongated through bore for passage of the shaft 232. The distal end of the shaft 232 having the collar 230 thereon translates within a proximal-distal cavity 240, while the proximal end of the shaft having a proximal head 236 translates within a proximal-distal cavity 242. Because the control rod 112' is rigidly fastened to the collar 230 which in turn is fastened to the shaft 232, movement of the shaft produces identical movement of the control rod.

With particular reference to FIG. 13C, an annular cam follower 244 surrounds the shaft 232 between the actuator 44' and the fasciotomy spring 234. The cam follower 244 includes a short slot (not numbered) within which extends a small pin 246 projecting laterally from the shaft 232. In the position illustrated, the actuator 44' is in a neutral position not in contact with the cam follower 244, which in turn is therefore biased in a proximal direction by the fasciotomy spring 234 as far as the pin 246 and slot permit. A second cam follower 250 surrounds the shaft 232 between the actuator 44' and the fasciotomy spring 234. A force-limiting spring 252 is concentrically constrained around the shaft 232 between the proximal head 236 and the second cam follower 250. As noted, the actuator 44' is in the neutral position out of contact with the second cam follower 250, and thus the force-limiting spring 252 remains uncompressed.

A user displaces the thumb pad of the actuator 44' in a proximal direction as indicated by arrow 260 in FIG. 13B, which pivots the actuator 44' and urges the cam follower 244 in a proximal direction. Compression of the fasciotomy spring 234 causes proportional displacement of the collar 230 and control rod 112', therefore opening the jaws of the tool. At a certain distance of travel, the collar 230 reaches the end of the cavity 240 and further movement of the control rod 112' is impeded, corresponding to the maximum opening distance of the jaws. However, because the cam follower 244 includes the linear slot in which the pin 246 travels, the actuator 44' can continue its movement forcing the cam follower 244 proximally against the compressive force of the spring 234. The user experiences a resistance to movement of the actuator 44' during this stage, which is an indication that the fasciotomy heater is activated. In particular, a tang 262 (FIG. 13C) on the actuator 44' eventually engages a fasciotomy switch 264 at the point that the fasciotomy spring 234 is being compressed. Although the circuitry is not shown, the switch 264 is supplied with current and when switched ON provides current to leads extending through the flexible shaft 36' to the distal end of tool and fasciotomy heating element.

Conversely, the user displaces the actuator 44' in a proximal direction as indicated by arrow 270 in FIG. 13C to close the jaws. A proximal face of the actuator 44' cams against the follower 250, which in turn acts against the force-limiting spring 252. As in the earlier embodiment, a minimal reaction force exists prior to the jaws closing and thus movement of the actuator 44' causes proportional movement of the control rod 112'. At the point that the jaws close over tissue, the force-limiting spring 252 determines the amount of pressure that may be applied to the tissue before further movement of the actuator 44' merely compresses the spring without moving the control rod 112'. Near the limit of travel of the actuator 44' in the direction of arrow 270, the tang 262 engages a weld/cut switch 272 mounted within the housing 140', thus actuating the welding and cutting heating elements at the distal end of the tool. The alternative control handle 38' further includes a detent 274 that acts in the same manner as the detent 212 described above and indicates to the user when the weld/cut function is ON and OFF.

Figure 14A:
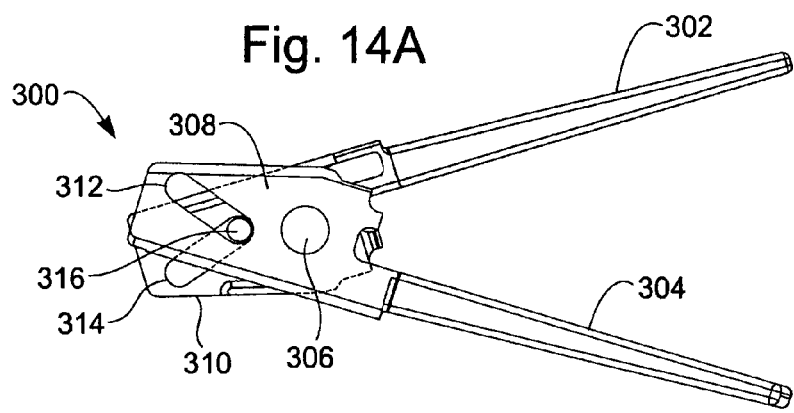
FIGS. 14A-14C are elevational views of pair of jaws in open and closed positions that illustrate a preferred jaw opening mechanism of the present invention.
Figure 14B:
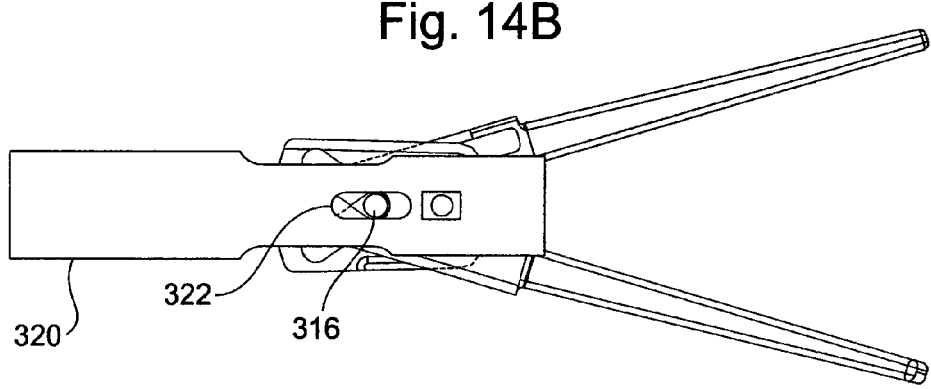
Figure 14C:
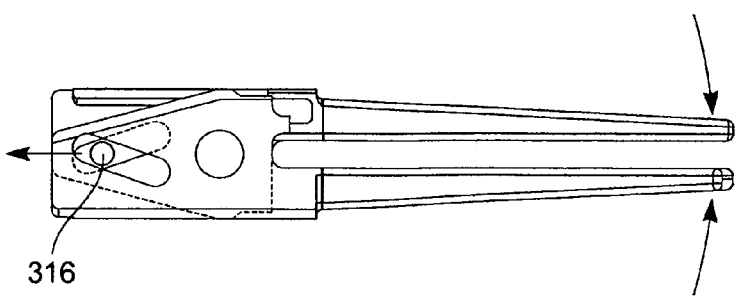

FIGS. 14A-14C illustrate a preferred linkage 300 between a control rod and the jaws for opening and closing the jaws. In the jaw opening mechanisms of the prior art, certain disadvantages were recognized that increase the overall size of the jaw assembly, increase the cost of construction, exposed electrical connections to wear, or sacrificed mechanical and electrical consistency by including excess sources of friction, and sacrificed electrical consistency by relying on moving mechanical connections for electrical continuity, for example. The exemplary linkage 300 and the associated "hard-wired" electrical connection reduces the overall size of the jaws assembly, reduces the number of components and associated cost and complexity, improves the robustness of the mechanics, and improves the mechanical and electrical reliability (i.e., consistency) of the device.

A pair of jaws 302, 304 are shown open in FIGS. 14A and 14B. Each jaw includes a through bore that is journalled about a shaft 306, such as the shaft stub 98 as seen in FIG. 5B. In this manner, proximal housings 308, 310 of the respective jaws pivot with respect to one another. An angled slot 312, 314 is provided in each pivot housings 308, 310. An actuating pin 316 extends into both of the angled slot 312, 314 and is connected to a proximal control rod (not shown). FIG. 14B illustrates the distal end of a tool shaft 320 that encompasses the pivot housings 308, 310. The tool shaft 320 includes a linear slot 322 within which the actuating pin 316 translates. The distal end of the tool shaft 320 shown is analogous to the shaft tip 54 seen in FIGS. 2 and 4.

FIG. 14C shows movement of the actuating pin 316 to the left which causes the jaws 302, 304 to close. That is, the pin 316 cams the angled slots 312, 314 such that their proximal ends come together as seen. Of course, the reverse movement of the actuating pin 316 causes the jaws to open again. Because of the simplicity of the mechanism, the overall size of the jaw assembly can be reduced so that it fits through a 5 mm inside diameter tube. Furthermore, the reduction in the number of parts obtains an equivalent reduced manufacturing time and complexity, for a lower manufacturing cost. The moving parts consist of the actuating pin 316 translating within the three slots, and the two jaws which pivot with respect one another. This reduces the sources of friction and thus improves mechanical reliability. Finally, the angle of the slots 312, 314 may be adjusted to change the actuation force required to open and close the jaws. That is, a shallower angle would necessitate a lower force from the control rod to actuate the jaws. The trade-off, of course is that the opening distance of the jaws is concurrently reduced.

Clearly, the dual- or tri-heating element function can be achieved in many different ways. The present invention broadly includes a heating element for cutting tissue and a heating element for welding tissue, and is not particularly limited to any one type of either apparatus. Examples include, but are not limited to two, three, or more heating elements, cutting and welding heating elements separately activated or connected in series or parallel, or both, heating elements on one or both jaws, etc. The form of the multiple heating elements is preferably chosen so that they are relatively close together and one reliably cuts and the other reliably welds a variety of tissue.

Optionally, the multiple heating elements are configured such that they operate substantially simultaneously and ensure good hemostasis of the welded tissue. The power applied and shape of the heating elements are chosen to ensure that inadvertent tissue charring or other such damage does not occur inadvertently during normal operation of the device. The primary clinical benefits of the heating elements of the present invention include but are not limited to balance of power outputs from cutter and welder(s) for consistently strong welds, as well as thermal efficiency for faster weld times.

It should be understood that the force-limiting function of the spring within the control handle can be achieved in many different ways. The present invention, in its broad interpretation, is not particularly limited to any one type of mechanism for limiting the closing force of the jaws, but is characterized by a force-limiting interface between the control actuator and the elongated jaws for limiting the magnitude of closing force of the jaws. Examples include, but are not limited to the aforementioned spring provided within the control handle, a similar spring provided distal to the control handle, a pressure transducer on the jaws which provides feedback to the user or other device for limiting the force applied by the jaws, compliant jaws, etc. The form of the force-limiting apparatus is preferably chosen to limit the pressure applied to tissue by the particular jaws. Optionally, the force-limiting apparatus is configured simply in a cost-effective manner. The force-limiting apparatus is chosen to ensure that crushing of tissue does not occur inadvertently during normal operation of the device.

Furthermore, aside from limiting the magnitude of force applied by the jaws, the present application contemplates applying force on the tissue within the jaws that is greater than a minimum but less than the force that would unduly damage the tissue. The minimum amount of force is determined such that an effective weld is created by clamping and heating the tissue. Accordingly, the minimum amount of force required depends on several factors, including the amount and duration of heat applied, the size and shape of the jaws, the jaw and boot material, the size and character of the tissue or vessel within the jaws, etc. In a preferred embodiment, a force-limiting mechanism interposed between the control actuator and the jaws is adapted to regulate the magnitude of closing force of the jaws to a value calibrated to ensure the heating element effectively welds tissue held within the facing surfaces of the elongated jaws.

While the tissue welding system described thus far is believed to be particularly effective, the present invention also provides a number of alternative jaws and clamping mechanisms which are each believed to be patentable in their own right. A number of these alternatives will now be described briefly with reference to FIGS. 15-48.

For example, the present application provides a number of embodiments for regulating the localized force applied to the tissue within the jaws. Several embodiments act to maintain parallelism of the jaws, which helps make the applied force, and thus applied heat, uniform from a proximal to a distal end of the jaws. Another configuration controls the gross movement of the jaws with respect one another such that they behave in a non-linear fashion relative to movement of a handle actuator. In short, the present application provides numerous configurations for controlling the applied force and displacement of the distal tissue welding jaws. It should be understood by the reader that unless they are mutually exclusive, any of these jaw or clamping configurations can be coupled with any of the aforementioned control handle/shaft embodiments. For example, if a particular jaw includes a malleable tissue contacting surface, it may also be used with the control handle 38 of FIGS. 11-12 which includes a pressure-limiting spring.

With reference now to FIGS. 15A-15B, a first embodiment of a force-limiting structure within a control handle 350 is shown. Only a portion of the control handle 350 is illustrated, and the remainder of the control handle may be similar to that described with respect to FIGS. 11-13. The control handle 350 incorporates an actuator 352 that pivots about a pin 354. A lever arm 356 projecting into the handle 350 from the actuator 352 engages a control rod 358. The control rod 358 extends distally through a flexible shaft 360 to open and close distal tissue welding jaws (not shown), such as described above. The lever arm 356 may be bifurcated, for example, such that its ends straddle the control rod 358 between a proximal ball 362a and a distal ball 362b. A spring 364 concentrically surrounds the control rod 358 and is interposed between the lever arm 356 and the proximal ball 362a.

When the actuator 352 is rotated in a clockwise direction, such as seen in FIG. 15A, the lever arm 356 moves in a leftward direction against the spring 364, which in turn acts against the proximal ball 362a. As long as the reaction force on the jaws is less than the spring constant, the spring 364 remains uncompressed and moves as a rigid body. This direction of travel of the control rod 358 corresponds to closing of the distal jaws. If the jaws close upon tissue, or are otherwise prevented from further closure, the reaction force through the control rod 358 eventually becomes greater than the spring constant, and the lever arm 356 compresses the spring 364 against the proximal ball 362a.

Although the lever arm 356 continues to move, it does not translate movement to the control rod 358 and the jaw force clamping the tissue remains constant. Conversely, counter-clockwise rotation of the actuator 352, such as seen in FIG. 15B, causes the lever arm 356 to travel to the right- and act directly on the distal ball 362b; Because the distal ball 362b is fixedly attached to the control rod 358, pivoting movement of the actuator 352 directly translates into linear displacement of the control rod, which opens the jaws. This arrangement is similar to the force-limiting configuration described above with respect to FIGS. 11-13.

In a slight variation to the embodiment of FIGS. 15A and 15B, the lever arm 356 itself may be formed as a spring in lieu of the coil spring 364. In such an alternative, the lever arm 356 is a metallic or molded plastic leaf spring that is bifurcated around the control rod 358. Application of a closing force eventually causes the lever arm 356 to bend, therefore limiting the applied clamping force at the jaws. To ensure that the lever arm 356 bends consistently at a predetermined force, it may be formed with a concavity (similar to a reed for a wind instrument) for added structural rigidity enabling it to resist buckling longer until reaching a discreet load.

FIGS. 16A and 16B illustrates an alternative variation of a force-limiting configuration. An actuator 370 includes a rigid portion, defined by a thumb lever 372 and a lever arm 374, that pivots about a pin 376. A second thumb lever 378 also pivots about the pin 376 and is connected via a coil spring 380 to the lever arm 374. Although not shown, a control rod attached to open and close distal tissue welding jaws is coupled to move with the distal end of the lever arm 374. Depressing the thumb lever 372 in a counter-clockwise direction as shown in FIG. 16A causes the lever arm 374 to translate to the right, corresponding to linear movement of the control rod to open the distal jaws. On the other hand, depressing the second thumb lever 378 in a clockwise direction as seen in FIG. 16B causes the lever arm 374 and control rod to translate to the left, and thus open the distal jaws. Eventually, a reaction force from the jaws transmitted from the control rod to the lever arm will be sufficient to cause the coil spring 380 to compress, thus effectively decoupling movement of the second thumb lever 378 from movement of the distal jaws. Again, the clamping force on the tissue remains constant after the spring 380 begins to compress.

FIGS. 17A and 17B illustrate an alternative force-limiting actuator 390 having a rigid portion defined by an extension 392 and a lever arm 394. The rigid portion pivots about a pin 396, about which also pivots a thumb lever 398 having wings extending in opposite directions. Depressing one of the wings of the thumb lever 398 in a counter-clockwise direction as indicated in FIG. 17A acts on the extension 392 which causes the lever arm 394 to translate to the right and move a control rod linearly (not shown). The control rod, in turn, opens the distal tissue welding jaws. Depressing the opposite wing in a clockwise direction as seen in FIG. 17B causes a leaf spring 400 to contact one side of the lever arm 394. As the lever arm 394 translates to the left, and pulls the control rod, the jaws close. Eventually, closure of the jaws on tissue results in a reaction force being transmitted through the control rod which resists further movement of the lever arm 394. If the user depresses the wing of the thumb lever 398 farther, the leaf spring 400 merely bends.

An alternative force-limiting structure provided within the control handle that is not specifically illustrated includes a pair of magnets that repel one another. For example, in FIGS. 17A and 17B the lever arm 394 and thumb lever 398 may carry magnets with like poles facing one another such that when the thumb lever 398 pivots in a clockwise direction the opposite magnets provide resistance against further closing motion.

Another variation of a force-limiting structure incorporated into a control handle is seen in FIG. 18. An actuator includes a rigid portion having a lever arm 410 and a perpendicular extension 412. The rigid portion pivots about a shaft 414 about which also pivots a thumb lever 416 having opposite wings. A pin or other such projection 418 extends perpendicularly from the right-hand wing of the thumb lever 416 so as to engage the extension 412. The distal ends of the right-hand wing and the extension 412 are connected by a coil spring 420. Depressing the right-hand wing of the thumb lever 416 causes the pin 418 to contact and pivot the extension 412 about the shaft 414, thus moving a control rod 422 connected to the lever arm 410. Depressing the left-wing of the thumb lever 416 rotates the extension 412 in a clockwise direction about the shaft 414 until such time as a reaction force through the control rod 422 and lever arm 410 causes the coil spring 420 to expand.

Instead of the interposition on a spring between a thumb lever and a control rod, a clutch may be provided which completely decouples relative movement therebetween. For example, FIG. 19 illustrates an arrangement similar to that shown in FIG. 18, but instead of the coil spring 420 a ball detent 430 is provided on the rigid portion of the actuator. The ball detent 430 engages the left-hand wing when the thumb lever 416 pivots in a counterclockwise direction. At a threshold reaction force, the ball detent 430 slips so that the thumb lever 416 no longer acts on the control rod.

Another variation of a clutch configuration is seen in FIG. 20. In this version, a toothed rack 440 is mounted on a proximal end of the control rod 442 within the control handle (represented by a frame 443). An actuator 444 includes a spring-loaded pin 446 that engages the toothed rack 440. Movement of the actuator 444 to the left or right causes equivalent movement of the toothed rack 440, and control rod 442. If tissue within the distal jaws causes the control rod 442 to stop moving, eventually the pin 446 moves upward against its spring and cams out of the teeth of the rack 440. A second spring 448 may be attached between the frame 443 and actuator 444 to provide a return force in one direction.

FIG. 21 illustrates an alternative configuration of a spring for use as a force-limiting member. In this embodiment, a tubular control rod 450 provides the spring itself. Namely, a laser cut spiral 452 in the control rod 450 results in a helical section designed to compress or extend upon a predetermined force being applied to the control rod. This configuration therefore eliminates a separate coil spring around the control rod. In a further alternative to forming a spring within the control rod 450, a segment or all of a control rod may be made from super-elastic material such as Nitinol which undergoes a phase transition and stretches after application of a threshold tensile force. Desirably, in the latter arrangement a separate rigid push rod may be provided to open the jaws in conjunction with the super-elastic pull rod which limits the force that can be applied when closing the jaws. In one particular embodiment, a 30 cm long super-elastic pull rod undergoes approximately 5% elongation (1.5 cm) without exceeding its elastic limit (usually 6% with Nitinol), which therefore permits further actuator travel without applying more force to the closed jaws. Again, with elastic force-limiting members, a constant force is applied to tissue between the jaws after they close.

FIG. 22A illustrates an alternative force-limiting configuration for a tissue welder of the present invention which is not located within a control handle 460. An actuator 462 includes a lever arm 464 that acts in opposite directions on two balls fixed to an actuator rod 466. The actuator rod extends into a flexible shaft 468 and is fixedly attached to a distal block 470 therein. A small flange 472 is also provided on the actuator rod 466. A proximal block 474 includes a through bore that receives the actuator rod 466. A control rod 476 is fixedly attached to the proximal block 474 and continues in a distal direction through a bore in the distal block 470. A coil spring 478 surrounds both the actuator rod 466 and control rod 476 in the area between the distal and proximal blocks 470, 474.

Rotation of the actuator 462 in the clockwise direction as shown causes the lever arm 464 to act on the proximal ball and translate the actuator rod 466 to the left. This movement pulls the distal block 470 to the left, as indicated and also through the spring 478 causes the proximal block 474 and control rod 476 to move leftward. Typically this movement corresponds to closure of distal tissue welding jaws. At some point, the jaws close or close on tissue and resist further leftward movement of the control rod 476. Further movement of the actuator rod 466 merely compresses the spring 478. This is the situation shown in FIG. 22A in which a space S is indicated between the flange 472 and the proximal block 474. Rotation of the actuator 462 in the opposite direction acts on the distal ball of the actuator rod 466 causing it to move distally to the right. In this case, the flange 472 acts directly on the proximal block 474 and pushes the control rod 476 an equivalent distance to the right (this is shown for the alternative configuration of FIG. 22B).

FIG. 22B shows a slight variation on the force-limiting configuration of FIG. 22A which incorporates not only a first coil spring 478 but also a second coil spring 480. The two springs 478, 480 provide two different spring rates such that regulation of closing of the distal jaws occurs in two stages. Namely, the first spring 478 compresses when the distal jaws provide a first reaction force. The user senses this resistance and thus knows when tissue is clamped between the jaws. Further compression of the spring 478 ultimately results in compression of the second spring 480, having a higher spring rate. The second spring 480 can be used to differentiate activation of a switch, for instance, to weld or for fasciotomy, or just as a detent to differentiate between grasping and welding.

Figure 23:
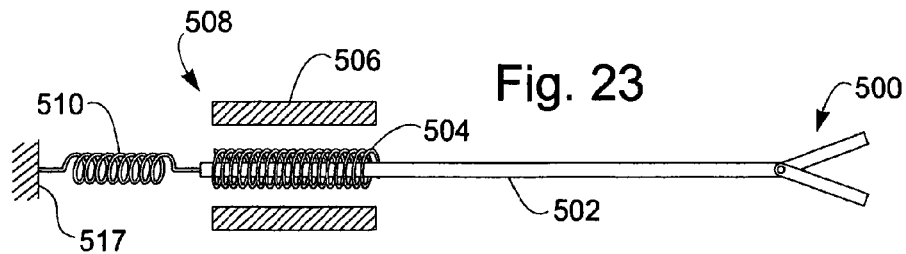
FIG. 23 is a schematic view of a solenoid for displacing a control rod and limiting the force applied thereby.

Now with reference to FIG. 23, a pair of tissue welding jaws 500 is shown schematically attached to the end of the control rod 502. A portion of the control rod has a voice coil 504 thereon surrounded by a magnet 506. This assembly provides an electromotive actuator 508 for translating the control rod 502 in proximal and distal directions upon running a current through the voice coil 504. In this embodiment, a return spring 510 connects the control rod 502 to a control handle, represented by a fixed point 512. The strength of the electromotive actuator 508 is desirably calibrated to be more than the minimum required to weld tissue within the jaws 500 but less than a force which would unduly damage the tissue. The strength of the electromotive actuator 508 can be controlled by choice of coil 504 or magnet 506, or by regulating the current supplied to coil. The electromotive actuator 508 may be arranged as a solenoid or voice coil, whichever provides the desired response.

Figures 24, 25:
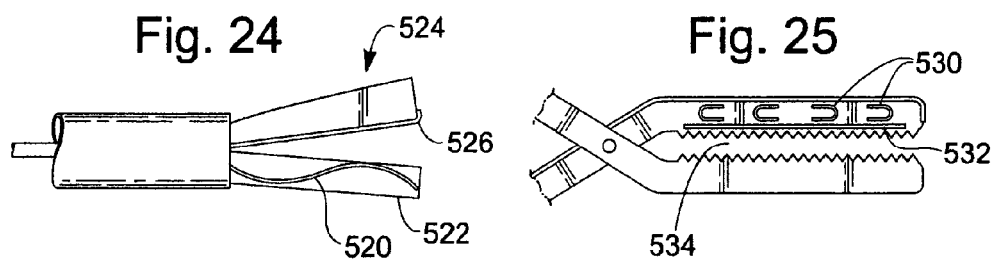
FIGS. 24-25, 26A, and 26B are schematic views of distal tissue welding jaws that are structured therein for limiting the amount force that can be applied thereby to tissue.

FIG. 24 illustrates a force-limiting leaf spring 520 provided within soft material 522 of one of the tissue welding jaws 524. A heating element 526 is illustrated on the opposite jaw. Closure of the jaws 524 with tissue therebetween eventually causes the leaf spring 520 to bend, thus limiting the amount of force that can be applied to the tissue.

In FIG. 25, a similar arrangement as that in FIG. 24 has a series of bi-metallic inserts 530 mounted within one of the jaws that includes the heating element 532. The bi-metallic inserts 530 are U-shaped and the two materials are chosen so that upon heating their differential expansion rates cause the inserts to straighten out. The jaws are arranged so that at their closest a gap 534 exists. Upon actuation of the heating element 532, the bi-metallic inserts 530 straighten out from their U-shaped configuration, thus forcing the heating element 532 against the tissue within the gap 534. Careful control of the dual materials of the bi-metallic inserts 530 and/or the amount of heat supplied by the heating element 532 ensures that proper welding occurs without tissue damage. In general, an elastic member(s) provided in one or both jaws is adapted to change shape at elevated temperatures. For example, instead of bi-metallic inserts 530, a U-shaped member formed of a shape memory alloy with a phase transition temperature adjusted to the maximum heating element temperature may be utilized.

Figures 26A, 26B:
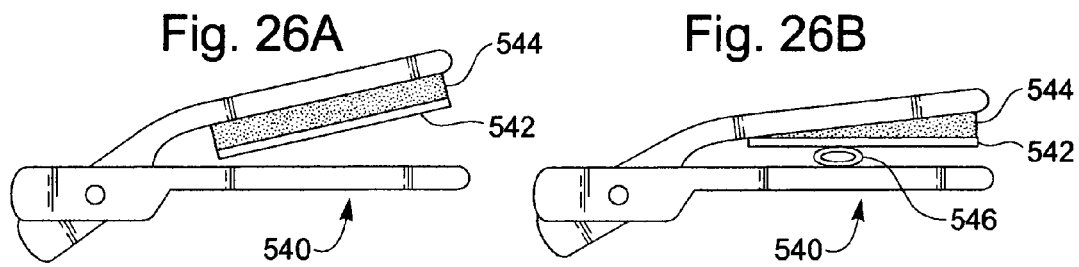

FIGS. 26A and 26B illustrate a still further version of an arrangement for limiting the amount of force applied to tissue that is incorporated within a pair of tissue welding jaws 540. A rigid tissue contacting plate 542 attaches to one of the jaws via an elastomeric layer 544 (the opposite jaw carries the heating element). FIG. 26B depicts compression of a blood vessel 546 within the jaws 540. At some point of jaw closure, the elastomeric layer 544 deforms to limit the amount of force applied to the vessel 546. In addition, the compliant character of the elastomeric layer 544 is such that it compresses more toward the proximal ends of the jaws 540 and thus helps maintain parallelism between the tissue contacting plate 542 and the opposite jaw. Stated another way, upon jaw closing the compliant middle layer 544 compresses unevenly such that the rigid tissue contacting plate 542 floats on its jaw 540 and helps even out clamping pressure on the vessel 546. This arrangement not only limits force but also helps ensure even heating of the vessel 546 in a proximal-distal direction.

Figure 27:
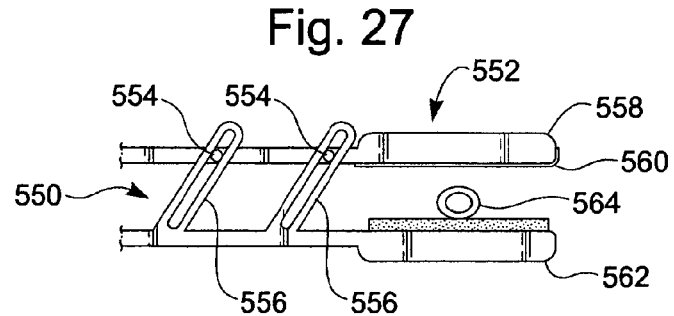
FIG. 27 is a schematic depiction of the mechanism for maintaining parallelism of tissue welding jaws.

FIG. 27 schematically illustrates a mechanism 550 for maintaining parallelism of a pair of jaws 552. Translation of a pair of pins 554 within angled guide brackets 556 ensures that a first jaw 558 having a heating element 560 thereon remains parallel to an opposite jaw 562. This results in more even heating of the vessel 564 between the jaws 552, at least in a proximal-distal direction. It should be noted here that the mechanism 550 for maintaining parallelism of the jaws 552 can be coupled with any of the force-limiting configurations disclosed herein.

FIG. 28 illustrates an arrangement for both limiting the force that is applied to tissue between a pair of jaws 570a, 570b and maintaining parallelism between the jaws. The proximal ends of the jaws 570a, 570b are illustrated at the distal end of a flexible shaft 572 that houses a control rod 574. Much like the movement mechanism seen in FIGS. 14A-14C the control rod 574 is connected to a pin 576 that translates in a proximal-distal line and acts on a pair of angled slots 578 formed in the jaws 570a, 570b. The jaws 570a, 570b are shown open with the pin 576 to the right end of the slots 578, and movement of the pin in a proximal direction closes the jaws. A jaw pivot shaft 580 is received within a transverse slot 582 formed in a first one of the jaws 570a, while the second jaw 570b pivots about the shaft 580 as a fixed point. That is, the position of the shaft 580 is fixed with respect to the second jaw 570b but translates along the slot 582 with respect to the first jaw 570a. A spring 584 normally maintains the shaft 580 at the bottom of the slot 582, and thus biases the proximal ends of the jaws together.

Upon closure of the jaws 570a, 570b on tissue, the proximal end of the second jaw 570b and the shaft 580 will be forced upward against the force of the spring 584, thus separating the proximal ends of the jaws. The reader will understand that the strength of the spring 584 may be calibrated to yield within a particular range of closing forces. For example, if the jaws 570a, 570b are being used to weld relatively small vessels or delicate tissue, the spring 584 has a slight stiffness, but application to larger vessels or more fibrous tissue may require a greater spring force. At the same time, other factors such as the shape of the jaws 570a, 570b or magnitude of heat applied may also affect the choice of spring 584.

Now with reference to FIG. 29, an actuator 590 configured to displace a control rod 592 at a non-linear rate is shown. The actuator 590 may be mounted to pivot about a shaft 594 within a control handle, such as was described previously. The proximal end of the control rod 592 carries a pin 596 positioned to travel within an arcuate cam slot 598 formed in an extension of the actuator 590. Through rotation of the actuator 590 about the shaft 594, the control rod 592 displaces as the pin 596 follows the cam slot 598, thus opening and closing distal tissue welding jaws. The reader will understand that, because of the shape of the cam slot 598 and its spatial relationship with respect to the shaft 594, the distance that the control rod 592 translates along its axis decreases as the actuator 590 rotates in a clockwise direction (indicated by arrow 599). Conversely, the distance the control rod 592 translates along its axis increases when the actuator 590 rotates in a counterclockwise direction. This variable or non-linear rate of travel of the control rod 592 may be beneficially coordinated with movement of the jaws so that as the jaws begin to come together their rate of closure decreases, or slows down. Conversely, as the jaws begin to open their rate of separation increases, or speeds up. This configuration may also be coupled with a force-limiting spring, for example, to automatically slow down the jaw closing phase and thus compress tissue with greater care.

Figure 30A:
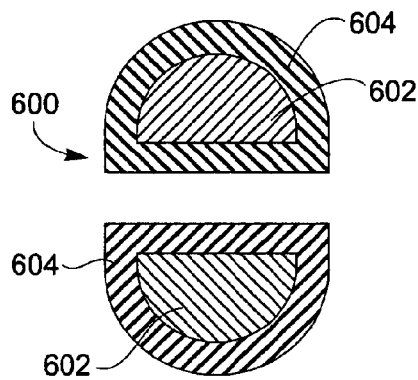
FIGS. 30A and 30B are cross-sectional views of symmetric tissue welding jaws.
Figure 30B:
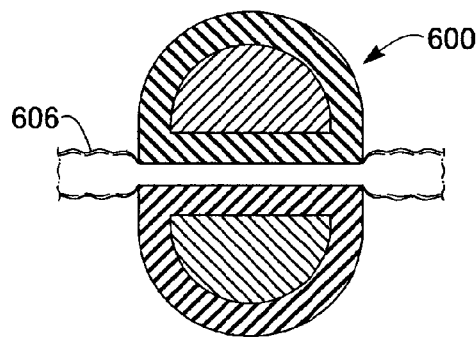

In addition to regulating the movement of the jaws, and their closing force, the construction of each of the jaws may be designed to focus heat or enhance their welding and severing efficiency. To understand several different configurations in this regard, FIGS. 30A and 30B illustrate a symmetric pair of jaws 600 each having an inner jaw 602 surrounded by a tissue-contacting boot 604. The symmetric jaws 600 are seen closing on a vessel 606 in FIG. 30B. A heating element is not shown, though any of the various configurations described herein may be coupled with the symmetric jaws 600 to weld and/or sever the vessel 606.

Figure 31A:
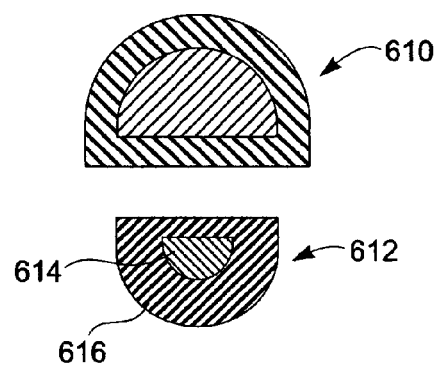
FIGS. 31A and 31B are cross-sectional views of asymmetric tissue welding jaws.
Figure 31B:
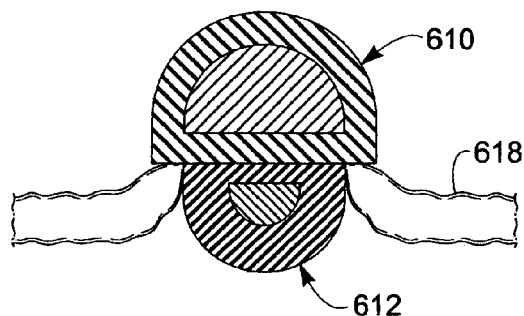

FIGS. 31A and 31B offer an alternative to the symmetric jaws 600, wherein a standard jaw 610 faces a relatively more narrow jaw 612. That is, the standard jaw 610 has a transverse width substantially greater than the narrow jaw 612. In this regard, the narrow jaw 612 has an inner jaw member 614 surrounded by a tissue-contacting boot 616, both are shown proportionately reduced in size from the standard jaw 610, preferably by at least 20%. When the jaws 610, 612 close on tissue, such as the vessel 618 seen in FIG. 31B, the reduced width of the narrow jaw 612 reduces the tissue contacting surface and causes a shearing action of sorts such that the vessel falls away on either side. This arrangement therefore helps sever the vessel 618 after it has been welded, and helps reduce tissue sticking to the jaws.

Figure 32:
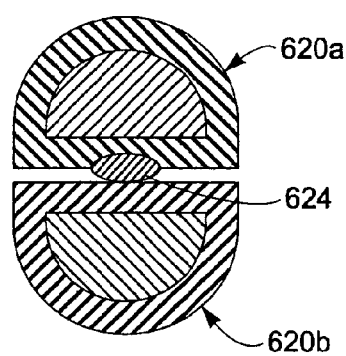
FIG. 32 is a cross-sectional view of symmetric tissue welding jaws, one of which has a heating element thereon.
Figure 33:
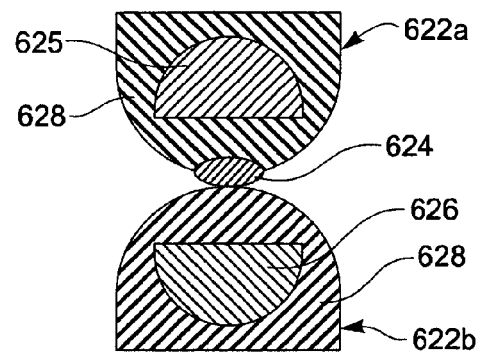
FIG. 33 is a cross-sectional view of symmetric tissue welding jaws having insulating boots that are reversed to present rounded tissue-contacting surfaces.

FIGS. 32 and 33 respectively illustrate a contrast between a standard pair of jaws 620a, 620b and an alternative pair 622a, 622b. The standard jaws 620a, 620b are similar to those shown in FIG. 30A, but also include a heating element 624 provided on a facing surface of the upper jaw 620a. The standard jaws 620a, 620b have generally semi-circular cross-sections with the flat sides facing one another. In contrast, the alternative jaws 622a, 622b have the same inner jaws 626 with their flat sides facing one another, but the surrounding tissue-contacting boots 628 are rotated 180° such that there curved sides face one another. Because the rounded surfaces of the boots 620 form the tissue-contacting surfaces, the transverse width of tissue that is clamped between the jaws is reduced. This focuses the pressure applied to the tissue during thermal tissue welding along more of a line centered on the heating element 624. Higher pressure at the heating element facilitates cutting of the tissue by both increasing heat transfer to the tissue and mechanical separation because of the higher pressure. The smaller tissue-contacting area also helps reduce tissue sticking to the jaws.

Figure 34A:
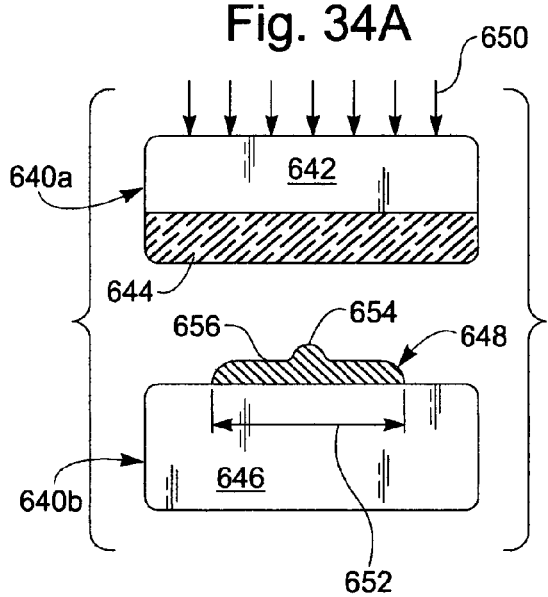
FIGS. 34A and 34B are schematic views of tissue welding jaws, one of which has a malleable facing surface and the other which has a contoured heating element thereon.
Figure 34B:
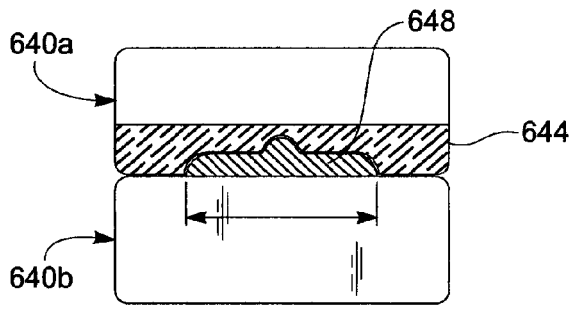

FIGS. 34A and 34B illustrate jaws 640a, 640b in open and closed positions, respectively, that incorporate several of the concepts disclosed above. A first jaw 640a includes a rigid portion 642 and a compliant or malleable pad 644 on its jaw facing surface. The second jaw 640b includes a rigid portion 646 supporting a contoured heating element 648 on its jaw facing surface. A plurality of force arrows 650 represent the application of uniform pressure to the upper side of the first jaw 640a, such as through the use of fluid-mechanics (e.g., pneumatics or hydraulics). Specifically, a fluid-mechanical driver (not shown) would be connected between the control actuator of the handle and the jaws 640a, 640b and is adapted to translate movement of the control actuator into movement of the jaws. When the jaws 640a, 640b close, as seen in FIG. 34B, the malleable pad 644 conforms to the contour of the heating element 648. The heating element has a transverse width 652 and a central protrusion 654 flanked by a pair of flat surfaces 656. The flat surfaces 656 function as welding elements, while the protrusion 654 acts as a cutting element because of its higher profile.

Figure 35:
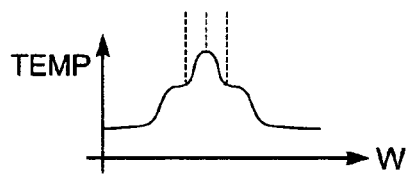
FIGS. 35 and 36 are graphs of temperature and pressure, respectively, across the width of tissue held within the jaws of FIGS. 34A and 34B.
Figure 36:
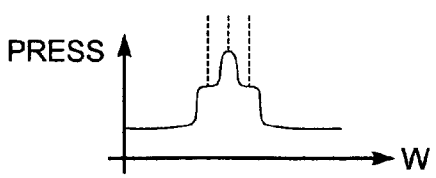

FIG. 35 is a graph schematically indicating the temperature profile within tissue held between the jaws 640a, 640b across their transverse width. The graph indicates a rise in the temperature in the tissue across the entire heating element 648, with a spike in the center corresponding to the protrusion 654. Assuming the material of the heating element 648 is uniform, the temperature of the heating element will also be uniform, but because of the higher pressure and thermal gradients in the tissue, the temperature in the tissue will be greater in the center. Of course, one potential alternative is to form the protrusion 654 as a different material than the rest of the heating element 648 so that the protrusion reaches a higher temperature. FIG. 36 is a graph schematically illustrating the pressure distribution within tissue held between the jaws 640a, 640b across their transverse width. Again, the pressure increases in the region of the heating element 648, and spikes in the center due to the raise protrusion 654.

Figure 37:
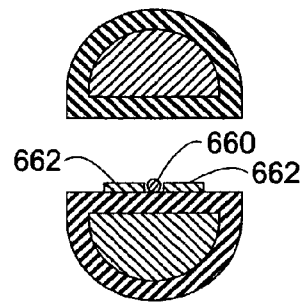
FIG. 37 is a cross-sectional view of an exemplary pair of tissue welding jaws, one of which has two heating elements thereon.
Figure 38:
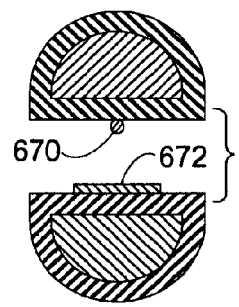
FIG. 38 is a cross-section sectional view of an alternative pair of tissue welding jaws both of which have heating element thereon.

A temperature and pressure distribution similar to that resulting from the jaw configuration of FIGS. 34A and 34B may be obtained using separate heating elements, such as shown in FIGS. 37 and 38. For instance, a narrow heating element 660 is positioned between a pair of flanking heating elements 662 on one of the jaws shown in FIG. 37. The temperature and pressure profiles obtained depend on how large the narrow heating element 660 is with respect to the flanking heating elements 662, and also on properties of the material, such as electrical resistance. It should also be understood that the flanking heating elements 662 may be actively heated, such as was described above, or they may be passively heated indirectly from heat generated by the narrow heating element 660. The jaws shown in FIG. 38 include a narrow heating element 670 on one jaw and a relatively wider heating element 672 on the opposite jaw. The narrow heating element 670 is positioned at the approximate transverse centerline of the wider heating element 672. When the jaws are brought together, the pressure and temperature are greatest between the two heating elements 670, 672, which therefore provides the tissue severing action. Once again, the wider heating element 672 may be actively or passively heated and acts as a tissue welding element. It should be noted that if the wider heating element 672 is actively heated, structure to electrically insulate the two elements during use will likely be provided.

Figure 39:
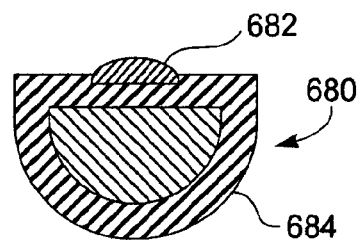
FIG. 39 is a cross-section sectional view of a tissue welding jaw having a heating element embedded within an insulating boot to provide smooth transitions therebetween.

FIG. 39 illustrates an alternative jaw 680 in which a heating element 682 is partially embedded within an outer boot 684. This smoother profile increases the transition angle between the heating element 682 and the boot 684 and thus helps enhance tissue release. More specifically, this smoother transition from heating element 682 to the insulating boot 684 reduces the amount of char that collects at the edge of the heating element, thereby reducing adhesion (sticking) of tissue to the jaws. Sticking may increase weld time and can result in damage to the weld band as the jaws are removed from the vessel.

Figure 40A:
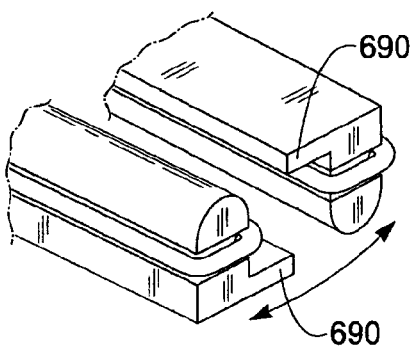
FIGS. 40A and 40B are schematic perspective views of a pair of tissue welding jaws having tissue severing flaps.
Figure 40B:
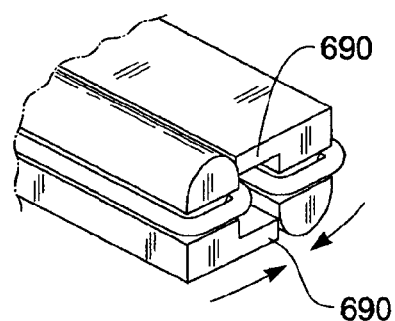

Another configuration for tissue welding jaws that helps release severed tissue is seen in FIGS. 40A and 40B. Each of the illustrated jaws includes a small flap 690 that projects toward the other jaw. The flap 690 may be formed as part of the insulating boot, or may extend from the more rigid inner jaw. Further, only one or both of the jaws may feature a flap 690. When the jaws close, as seen in FIG. 40B, the flaps 690 overlap to the side of the opposite jaw and push the vessel or tissue off of the jaws upon completion of the weld. This reduces weld time and sticking.

Figure 41A:
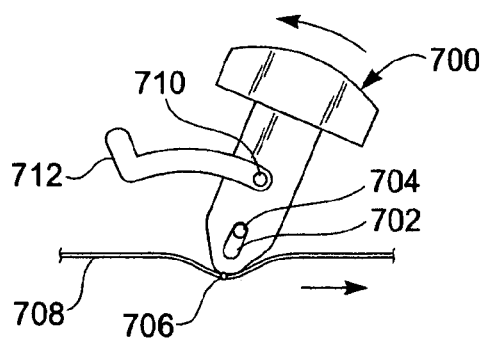
FIGS. 41A and 41B, and 42A and 42B are schematic views of alternative actuator toggles each having a mechanism for locking the toggle at one end of its travel.

The present invention also contemplates a number of alternative control mechanisms that enhance ergonomics or user-friendliness of the aforementioned devices. For example, in FIGS. 41A and 41B a locking feature in a toggle switch is provided so that the user need not maintain pressure on the jaws during the welding/severing process. A toggle or actuator 700 includes a small slot 702 that pivots and translates with respect to a shaft 704 fixed on a control handle (not shown). A lower end of the actuator 700 is secured at a point 706 to a flexible (e.g., Nitinol) control wire 708. The movement of the control wire 708 is seen in the two figures relative to movement of the actuator 700. The actuator includes a small pin 710 that translates within an L-shaped slot 712 formed as part of the control handle. FIG. 41A shows the actuator 700 in a position wherein the pin 710 is at the end of the long portion of the slot 712, and corresponds to the jaw open state of the device. In addition, the actuator 700 is biased so that the shaft 704 is normally at the top of the slot 702.

Figure 41B:
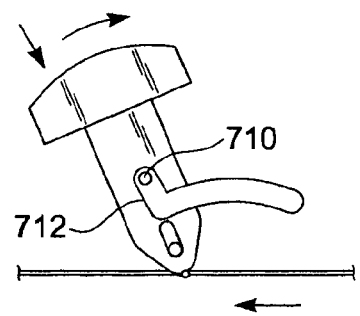

Upon rotation of the actuator 700 in the counter-clockwise direction, the pin 710 translates along the channel 712 into the position shown in FIG. 41B by virtue of the spring bias on the actuator 700. The pin 710 remains in the short, angled portion of the channel 712 while the jaws are closed and the tissue is being welded. The user must first depress the actuator downward to release the actuator 700 and open the jaws.

Figure 42A:
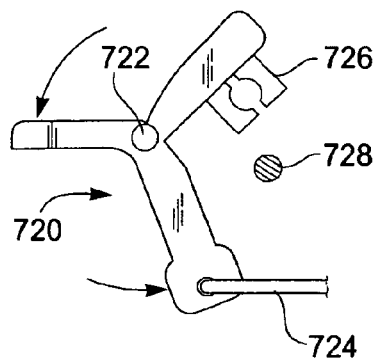
Figure 42B:
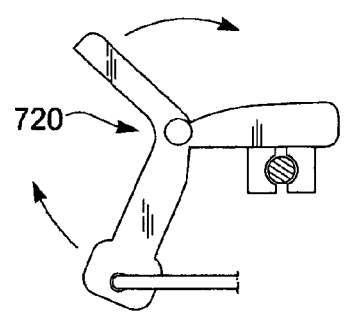

Another arrangement for locking an actuator 720 during the welding/severing phase is seen in FIGS. 42A and 42B. The actuator pivots about a shaft 722 within a control handle (not shown) and translates a control rod 724. A locking feature 726 is provided on an extension of the actuator 720 to engage a pin 728 fixed in the control handle. As seen in FIG. 42B, the actuator 720 may be locked in a clockwise position corresponding to the jaws being closed.

Figure 43A:
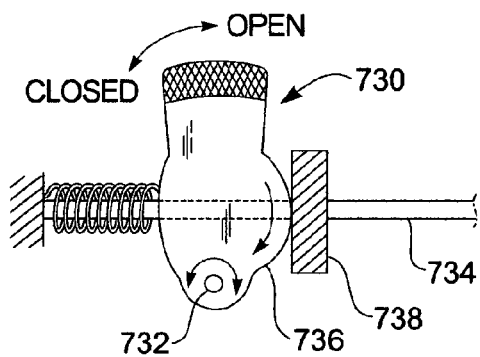
FIGS. 43A and 43B are schematic views of an actuator toggle and cam surface that acts on a control rod to angle the distal tissue welding jaws for fasciotomy.
Figure 43B:
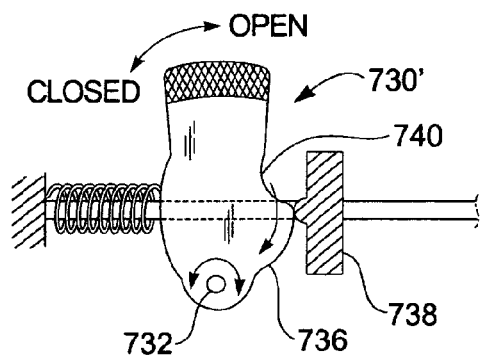
Figure 44:
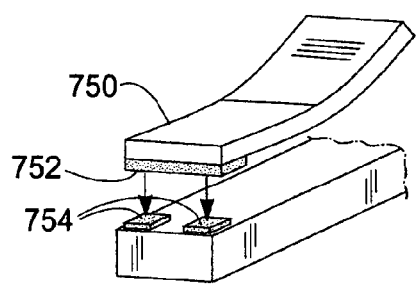
FIG. 44 shows a toggle or actuator.

An actuator specially designed to facilitate fasciotomy can be understood by comparing FIGS. 43A and 43B. The actuator 730 in FIG. 43A is similar to those described above with respect to FIGS. 11-13, and pivots about a shaft 732 fixed with respect to a control handle (not shown). The actuator 730 includes a through bore that receives a control rod 734 leading to distal tissue welding jaws. As the actuator 730 pivots in a clockwise direction as shown, a cam lobe 736 acts on a cam follower 738 attached to the control rod 734. The round profile of the cam lobe 736 pushes the follower 738 and rod 734 distally to the right to fully open the jaws.

FIG. 43B illustrates a modified actuator 730' that includes a recessed region 740 in the upper part of the cam lobe 736. As the actuator 730' continues rotating in a clockwise direction, the jaws open but eventually the cam follower 738 reaches the recess 740 and translates a small distance in the opposite direction to slightly close the jaws. After the actuator 730' has pivoted its full extent, the user may actuate a switch for fasciotomy. Because the cam follower 738 has retreated proximally a small distance, the jaws are not fully open so that there is less interference with the surrounding tissue cavity and more maneuverability of the jaws. The angle at which the jaws remain open during fasciotomy may be optimized based on the contour of the recess 740.

Fasciotomy using the tissue welding jaws of the present invention may also be enhanced by uneven control of one jaw with respect to the other. That is, much like the design seen in FIGS. 43A and 43B, there are other mechanisms for controlling the angle of the jaw having the cutting element thereon so that it more effectively faces the fascia to be cut. For example, the exemplary movement mechanism described above with respect to FIG. 4 may be modified so that the hot jaw 40 assumes an angle that facilitates fasciotomy. Namely, the angled slots 68 may be angled differently such that linear movement of the yolk 114 translates and unequal jaw opening motion. The hot jaw may be opened up to a steeper angle than the cold jaw. Another contemplated mechanism is an asymmetric two-bar linkage system such that the jaws open unevenly.

Figure 45:
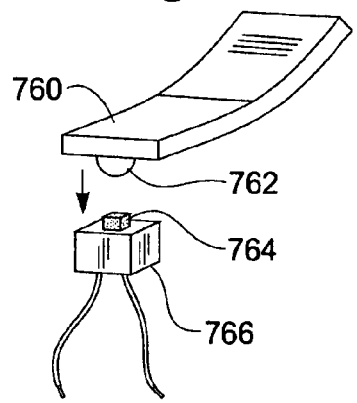
FIG. 45 shows a safety interlock.
Figure 46:
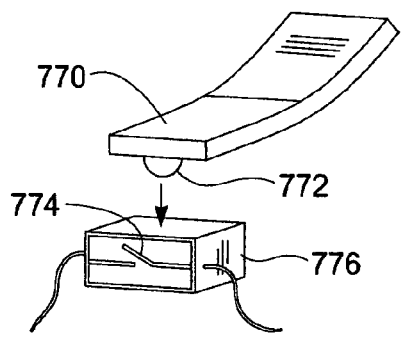
FIG. 46 shows another alternative wherein an actuator carries a protrusion that acts on a leaf spring to close a safety interlock circuit.

The present invention also contemplates a variety of means for activating safety interlocks for the electric circuits for the heating elements for welding, severing, or fasciotomy, such that the heating elements can only be actuated upon movement of the control actuator to fully close the jaws. For example, FIG. 44 discloses a toggle or actuator 750 having a conductive strip 752 on an underside positioned to contact and connect two pads 754 mounted within a control handle (not shown). Connecting the two pads 754 closes a safety interlock circuit such that another switch may then be actuated to energize the welding/severing heating elements. In this way, the user cannot energize the heating elements without the actuator being depressed, corresponding to the jaws being closed. An alternative arrangement of a safety interlock is seen in FIG. 45 wherein an actuator 760 carries a protrusion 762 positioned to contact the moving element 764 of a microswitch 766. Actuating the microswitch 766 enables separate activation of a heating element. Finally, FIG. 46 shows a third alternative wherein an actuator 770 carries a protrusion 772 that acts on a leaf spring 774 to close a safety interlock circuit. The leaf spring 774 may be enclosed or embedded by a fluid seal 776, such as a silicone membrane.

Figure 47A:
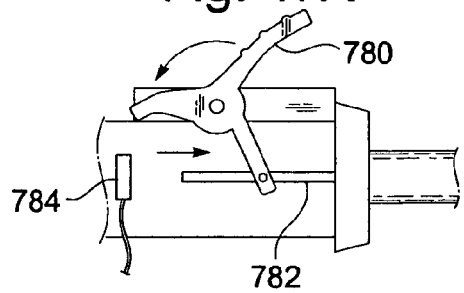
FIGS. 47A-47B show another safety interlock.
Figure 47B:
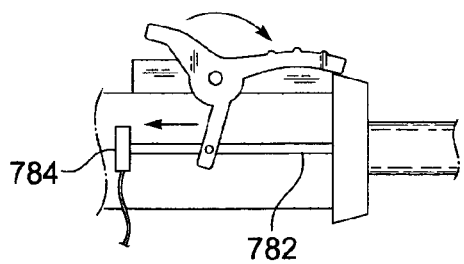
Figure 48A:
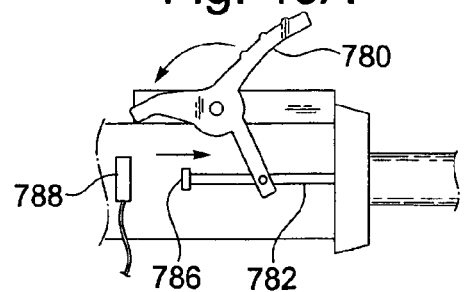
FIGS. 48A-48B show another safety interlock.
Figure 48B:
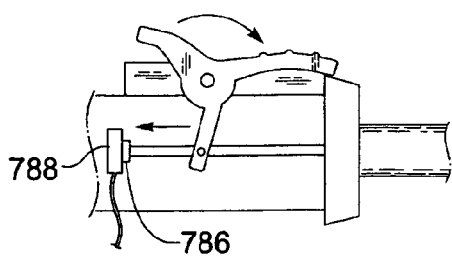

Two other safety interlock configurations are illustrated in FIGS. 47 and 48. In both of these, an actuator 780 pivots to translate a control rod 782, as has been previously described. In FIGS. 47A and 47B the control rod 782 eventually actuates a microswitch 784 at its proximal-most travel. The microswitch 74 may be part of a safety interlock circuit, or may be the heating element activation switch. In FIGS. 48A and 48B, the control rod 782 carries a conductive strip 786 that contacts a conductive pad 788 at the proximal end of its travel. In this embodiment, the control rod 782 is conductive and itself forms a part of a safety interlock circuit.

It will also be appreciated by those of skill in the relevant art that various modifications or changes may be made to the examples and embodiments described without departing from the intended scope of the invention. In this regard, the particular embodiments of the invention described herein are to be understood as examples of the broader inventive concept disclosed.

What is claimed is:

1. A surgical method of severing a target tissue while welding the severed ends using a surgical apparatus, the surgical apparatus comprising a shaft and first and second jaws extending from a distal end of the shaft, wherein the first jaw is relatively movable with respect to the second jaw; the surgical apparatus further comprising a first electrode and a second electrode electrically connected in series, wherein the first electrode is operatively associated with one of the first and second jaws and is adapted to weld tissue, and wherein the second electrode is operatively associated with one of the first and second jaws and is adapted to sever tissue, the method comprising:

welding and severing a target tissue by:
  closing the jaws upon the target tissue; and
  electrically energizing the first and second electrodes to form a welded region in the target tissue and sever the target tissue within the welded region.

2. The method of claim 1, further comprising maintaining parallelism between the jaws during the act of closing the jaws upon target tissue.

3. The method of claim 1, wherein the surgical apparatus further includes a control handle having a control actuator for opening and closing the jaws, and structure between the control actuator and the jaws for completely decoupling relative movement of the control actuator and the jaws at a predetermined closing force, the method comprising:
  during the act of closing the jaws upon the target tissue, closing the jaws until the predetermined closing force has been reached so that movement of the jaws is decoupled from further movement of the control actuator.

4. The method of claim 1, further comprising:
  filtering gas created by the act of welding and severing a target tissue before it is released to (i) an interior region of a control handle connected to the shaft or (ii) an environment local to the surgical apparatus.

5. The method of claim 1, wherein the surgical apparatus further includes a control handle having a control actuator for opening and closing the jaws, and structure between the control actuator and the jaws for influencing relative movement of the control actuator and the jaws at a predetermined closing force, the method comprising:
  during the act of closing the jaws upon the target tissue, closing the jaws until the predetermined closing force has been reached so that the closing force applied by the jaws on the target tissue remains constant even with further movement of the control actuator.

6. The method of claim 1, wherein the act of welding and severing a target tissue further comprises:
  limiting the magnitude of a closing force the jaws impart to the target tissue to a value calibrated to ensure the second electrode effectively severs and the first electrode effectively welds tissue held within facing surfaces of the jaws within a predetermined time frame.

7. The method of claim 6, wherein the predetermined time frame is of about 5 seconds or less.

8. The method of claim 6, wherein the act of limiting the magnitude of closing force of the jaws comprises:
  regulating the magnitude of closing force of the jaws to between about 1-3 lbs (0.45-1.36 kg).

9. A surgical method of severing a target tissue while welding the severed ends using a surgical apparatus, the surgical apparatus comprising an elongated body having a distal end and a proximal end; first and second jaws operably extending from the distal end, at least one of the first and second jaw configured to move with respect to the elongated body; a control handle operably connected to the proximal end, the control handle comprising a control actuator that causes relative movement of the first jaw with respect to the second jaw; a first heating element disposed on the first jaw and a second heating element disposed on one of the first and second jaws and wherein at least a portion of the first heating element comprises two welding portions that are spaced apart from one another and electrically connected in parallel, the method comprising:

welding and severing a target tissue by:
  closing the jaws upon the target tissue; and
  electrically energizing the first heating element and second heating element to form a welded region in the target tissue and sever the target tissue within the welded region.

10. The method of claim 9, further including:
  maintaining parallelism between the jaws during the act of closing the jaws upon target tissue.

11. The method of claim 9, wherein the surgical apparatus further includes structure between the control actuator and the jaws for completely decoupling relative movement of the control actuator and the jaws at a predetermined closing force, the method comprising:
  during the act of closing the jaws upon the target tissue, closing the jaws until the predetermined closing force has been reached so that movement of the jaws is decoupled from further movement of the control actuator.

12. The method of claim 9, further comprising:
  filtering gas created by the act of welding and severing a target tissue before it is released to (i) an interior region of the control handle connected to the elongated body or (ii) an environment local to the surgical apparatus.

13. The method of claim 9, wherein the surgical apparatus further includes structure between the control actuator and the jaws for influencing relative movement of the control actuator and the jaws at a predetermined closing force, the method comprising:
  during the act of closing the jaws upon the target tissue, closing the jaws until the predetermined closing force has been reached so that the closing force applied by the jaws on the target tissue remains constant even with further movement of the control actuator.

14. The method of claim 9, wherein the act of welding and severing a target tissue further comprises:
  limiting the magnitude of a closing force the jaws impart to the target tissue to a value calibrated to ensure the second heating element effectively severs and the first heating element effectively welds tissue held within facing surfaces of the jaws within a predetermined time frame.

15. The method of claim 14, wherein the predetermined time frame is of about 5 seconds or less.

16. The method of claim 14, wherein the act of limiting the magnitude of closing force of the jaws comprises:
  regulating the magnitude of closing force of the jaws to between about 1-3 lbs (0.45-1.36 kg).

17. A surgical method of severing a target tissue while welding the severed ends using a surgical apparatus, the surgical apparatus comprising a shaft having a proximal region and a distal region; first and second jaws extending from the distal region of the shaft, wherein the first jaw is relatively movable with respect to the second jaw; a first electrode portion operatively associated with one of the first and second jaws and is adapted to weld tissue; a second electrode portion operatively associated and fixedly attached with one of the first and second jaws and configured to have a different electrical resistance value than the first electrode portion, the second electrode portion is adapted to sever tissue upon the application of current therethrough; and a control handle operably connected to the proximal region of the shaft; wherein the first and second electrode portions are connected in series, the method comprising:

welding and severing a target tissue by:
    closing the jaws upon the target tissue; and
    electrically energizing the first electrode portion and second electrode portion to form a welded region in the target tissue and sever the target tissue within the welded region.

18. The method of claim 17, wherein the first electrode portion comprises two welding portions that are spaced apart from one another and electrically connected in parallel; wherein the control handle further comprises a control actuator for opening and closing the jaws, and wherein the surgical apparatus further comprises structure between the control actuator and the jaws for influencing relative movement of the control actuator and the jaws at a predetermined closing force, the method comprising:
    during the act of closing the jaws upon the target tissue, closing the jaws until the predetermined closing force has been reached so that the closing force applied by the jaws on the target tissue remains constant even with further movement of the control actuator.

19. The method of claim 17, wherein the act of welding and severing the target tissue further comprises:
    limiting the magnitude of a closing force the jaws impart to the target tissue to a value calibrated to ensure the second electrode portion effectively severs and the first electrode portion effectively welds tissue held within facing surfaces of the jaws within a predetermined time frame.

20. The method of claim 19, wherein the predetermined time frame is of about 5 seconds or less.

21. The method of claim 19, wherein the act of limiting the magnitude of closing force of the jaws comprises:
    regulating the magnitude of closing force of the jaws to between about 1-3 lbs (0.45-1.36 kg).

* * * * *